(12) United States Patent
Shoichet et al.

(10) Patent No.: US 8,629,197 B2
(45) Date of Patent: Jan. 14, 2014

(54) CHEMICALLY PATTERNED HYDROGELS, MANUFACTURE AND USE THEREOF

(76) Inventors: Molly Shoichet, Toronto (CA); Jordan Wosnick, Toronto (CA); Ryan Wylie, Toronto (CA)

(*) Notice: Subject to any disclaimer, the term of this patent is extended or adjusted under 35 U.S.C. 154(b) by 939 days.

(21) Appl. No.: 12/082,002

(22) Filed: Apr. 7, 2008

(65) Prior Publication Data

US 2008/0286360 A1 Nov. 20, 2008

Related U.S. Application Data

(60) Provisional application No. 60/910,447, filed on Apr. 5, 2007.

(30) Foreign Application Priority Data

Apr. 5, 2007 (CA) .................................... 2584087

(51) Int. Cl.
| | |
|---|---|
| *C08F 2/46* | (2006.01) |
| *C08J 3/28* | (2006.01) |
| *G01N 33/52* | (2006.01) |
| *C07D 407/00* | (2006.01) |

(52) U.S. Cl.
USPC ............... 522/86; 522/904; 522/35; 435/7.4; 435/7.1; 435/23; 549/400; 549/401; 549/402; 424/400; 424/484; 424/486; 424/487

(58) Field of Classification Search
USPC ............... 435/7.4, 7.1, 23; 524/916; 424/400, 424/484, 486, 487; 549/400, 401, 402; 522/86, 904
See application file for complete search history.

(56) References Cited

U.S. PATENT DOCUMENTS

| | | | | |
|---|---|---|---|---|
| 6,392,089 | B1* | 5/2002 | Falvey et al. .................. | 562/400 |
| 7,588,906 | B2* | 9/2009 | Brueggemeier et al. ....... | 435/7.4 |
| 2010/0207078 | A1* | 8/2010 | Marder et al. ................ | 252/586 |

OTHER PUBLICATIONS

Corrie, J. E. T., Furuta, T., Givens, R., Yousef, A. L. and Goeldner, M. (2005) Photoremovable Protecting Groups Used for the Caging of Biomolecules, in Dynamic Studies in Biology: Phototriggers, Photoswitches and Caged Biomolecules (eds M. Goeldner and R. S. Givens), pp. 1-94.*

Albrecht, D. R.; Underhill, G. H.; Wassermann, T. B.; Sah, R. L.; Bhatia, S. N., "Probing the Role of Multicellular Organization in Three-Dimensional Microenvironments," Nature Methods 2006, 3, 369-375.

Allen, R.; Nielson, R.; Wise, D. D.; Shear, J. B., "Catalytic Three-Dimensional Protein Architectures," Anal. Chem. 2005, 77, 5089-5095.

Ando, H.; Furuta, T.; Tsien, R. Y.; Okamoto, H., "Photo-Mediated Gene Activation Using Caged RNA/DNA in Zebrafish Embryos," Nature Genetics 2001, 28, 317-325.

(Continued)

*Primary Examiner* — Sanza McClendon
(74) *Attorney, Agent, or Firm* — Woodcock Washburn, LLP

(57) ABSTRACT

A chemically patterned modified hydrogel formed from a modified hydrogel is provided. The hydrogel is conjugated with a multiphoton photocleavable molecule. The molecule has a multiphoton-labile protective group and a protected group. The protective group is cleavable upon multiphoton excitation to deprotect the protected group, without substantial polymerization of the hydrogel. The chemically patterned modified hydrogel is formed by exposing the modified hydrogel to multiphoton excitation to deprotect a portion of the protected groups.

21 Claims, 8 Drawing Sheets

(56) References Cited

OTHER PUBLICATIONS

Basu, S.; Cunningham, L. P.; Pins, G. D.; Bush, K. A.; Taboada, R.; Howell, A. R.; Wang, J.; Campagnola, P. J., "Multiphoton Excited Fabrication of Collagen Matrixes Cross-Linked by a Modified Benzophenone Dimer: Bioactivity and Enzymatic Degradation," Biomacromolecules 2005, 6, 1465-1474.

Basu, S.; Wolgemuth, C. W.; Campagnola, P. J., "Measurement of Normal and Anomalous Diffusion of Dyes within Protein Structures Fabricated Via Multi-photon Excited Cross-Linking," Biomacromolecules 2004, 5, 2347-2357.

Cumpston, B. H., et al., "Two-Photon Polymerization Initiators for Three-Dimensional Optical Data Storage and Microfabrication," Nature 1999, 398, 51-54.

Denk, W.; Strickler, J. H.; Webb, W. W., "Two-Photon Laser Scanning Fluorescence Microscopy," Science 1990, 248, 73-76.

Diaspro, A.; Chirico, G.; Collini, M. Q., "Two-Photon Fluorescence Excitation and Related Techniques in Biological Microscopy," Rev. Biophys. 2005, 38, 97-166.

Eckardt, T.; Hagen, V.; Schade, B.; Schmidt, R.; Schweitzer, C.; Bendig, J., "Deactivation Behavior and Excited-State Properties of (Coumarin-4-yl)methyl Derivatives. 2. Photocleavage of Selected (Coumarin-4-yl)methyl-Caged Adenosine Cyclic 3',5'-Monophosphates with Fluorescence Enhancement," J. Org. Chem. 2002, 67, 703-710.

Flaim, C. J.; Chien, S.; Bhatia, S. N., "An Extracellular Matrix Microarray for Probing Cellular Differentiation." Nature Methods 2005, 2, 119-125.

Furuta, T.; Wang, S. S.-H.; Dantzker, J. L.; Dore, T. M.; Bybee, W. J.; Callaway, E. M.; Denk, W.; Tsien, R. Y., "Brominated 7-Hydroxycoumarin-4-ylmethyls: Photolabile Protecting Groups with Biologically Useful Cross-Sections for Two Photon Photolysis," Proc. Natl. Acad. Sci. USA 1999, 96, 1193-1200.

Goard, M.; Aakalu, A.; Fedoryak, O. D.; Quinonez, C.; St. Julien, J.; Poteet, S. J.; Schuman, E. M.; Dore, T. M., "Light-Mediated Inhibition of Protein Synthesis," Chem. Biol. 2005, 12, 685-693.

Hahn, M. S.; Miller, J. S.; West, J. L., "Three-Dimensional Biochemical and Biomedical Patterning of Hydrogels for Guiding Cell Behavior," Adv. Mater. 2006, 18, 2679-2684.

Helmchen, F.; Denk, W., "Deep Tissue Two-Photon Microscopy," Nature Methods 2005, 2, 932-940.

Hill, R. T.; Lyon, J. L.; Allen, R.; Stevenson, K. J.; Shear, J. B., "Microfabrication of Three-Dimensional Bioelectronic Architectures," J. Am. Chem. Soc. 2005, 127, 10707-10711.

Kaehr, B.; Allen, R.; Javier, D. J.; Currie, J.; Shear, J. B., "Guiding Neuronal Development with in situ Microfabrication," Proc. Natl. Acad. Sci. USA 2004, 101, 16104-16108.

Kuebler, S. M.; Braun, K. L.; Zhou, W.; Cammack, J. K.; Yu, T.; Ober, C. K.; Marder, S. R.; Perry, J. W., "Design and Application of High-Sensitivity Two-Photon Initiators for Three-Dimensional Microfabrication," J. Photochem. Photobiol. A 2003, 158, 163.

Lin, W.; Lawrence, D. S., "A Strategy for the Construction of Caged Diols Using a Photolabile Protecting Group," J. Org. Chem. 2002, 67, 2723-2726.

Lu, M.; Fedoryak, O. D.; Moister, B. R.; Dore, T. M., "Bhc-Diol as a Photolabile Protecting Group for Aldehydes and Ketones," Org. Lett. 2003, 5, 2119.

Lu, Y.; Hasegawa, F.; Goto, T.; Ohkuma, S.; Fukuhara, S.; Kawazu, Y.; Totani, K.; Yamashita, T.; Watanabe, T., "Highly Sensitive Two-Photon Chromophores Applied to Three-Dimensional Lithographic Microfabrication: Design, Synthesis and Characterization Towards Two-Photon Absorption Cross Section," J. Mater. Chem. 2004, 14, 75.

Luo, Y.; Shoichet, M. S., "Light-Activated Immobilization of Biomolecules to Agarose Hydrogels for Controlled Cellular Response," Biomacromolecules 2004, 5, 2315-2323.

Luo, Y.; Shoichet, M. S., "A Photolabile Hydrogel for Guided Three-Dimensional Cell Growth and Migration," Nature Materials 2004, 3, 249-235.

Perdicakis, B.; Montgomery, H. J.; Abbott, G. L.; Fishlock, D.; Lajoie, G. A.; Guillemette, J. G.; Jervis, E., "Photocontrol of Nitric Oxide Production in Cell Culture Using a Caged Isoform Selective Inhibitor," Bioorg. Med. Chem. 2005, 13, 47.

Rubart, M., "Two-Photon Microscopy of Cells and Tissue," Circ. Res. 2004, 95, 1154-1166.

Schade, B.; Hagen, V.; Schmidt, R.; Herbrich, R.; Krause, E.; Eckardt, T.; Bendig, J., "Deactivation Behavior and Excited-State Properties of (Coumarin-4-yl)metyl Derivatives. 1. Photocleavage of (7-Methoxycoumarin-4-yl)methyl-Caged Acids with Fluorescence Enhancement," J. Org. Chem. 1999, 64, 9109-9117.

Suzuki, A. Z.; Watanabe, T.; Kawamoto, M.; Nishiyama, K.; Yamashita, H.; Ishii, M.; Iwamura, M.; Furuta, T., "Coumarin-4-ylmethoxycarbonyls as Phototriggers for Alcohols and Phenols," Org. Lett. 2003, 5, 4867-4870.

Svoboda, K.; Yasuda, R., "Principles of Two-Photon Excitation Microscopy and Its Applications to Neuroscience," Neuron 2006, 50, 823-839.

Zipfel, W. R.; Williams, R. M.; Webb, W. W., "Nonlinear Magic: Multiphoton Microscopy in the Biosciences," Nat. Biotechnol. 2003, 21, 1369-1377.

Musoke, P.; Shoichet, M. S., "Anisotropic Three-Dimensional Peptide Channels Guide Neurite Outgrowth within a Biodegradable Hydrogel Matrix," Biomed. Mater. 2006, 1, 162.

Momotake et al, "The nitrodibenzofuran chromophore: a new caging group for ultra-efficient photolysis in living cells" Nature Methods, Jan. 2006, 3(1), 35-40.

Zhao et al, "New Caged Coumarin Fluorophores with Extraordinary Uncaging Cross Sections Suitable for Biological Imaging Applications", JACS, Published on web Mar. 2004, 126, 4653-5663.

* cited by examiner

US 8,629,197 B2

CHEMICALLY PATTERNED HYDROGELS, MANUFACTURE AND USE THEREOF

REFERENCE TO RELATED APPLICATION

This application claims benefit of U.S. Provisional Application No. 60/910,447, filed Apr. 5, 2007 and to Canadian Application No. 2,584,087, filed Apr. 5, 2007, the entirety of which are incorporated herein by reference.

FIELD

The present invention relates to the field of three-dimensional patterning of hydrogels.

BACKGROUND

Multiphoton excitation or absorption is the near simultaneous absorption of two or more photons to reach a reactive, excited state that is energetically inaccessible by the absorption of a single photon of the same energy. Multiphoton excitation, an important depth-sectioning tool in fluorescence microscopy,[1,2] relies on the large power density present at the focal point of a pulsed laser to excite chromophores using two or more low-energy photons. The process can be thought of as the near-simultaneous absorption of two or more photons by a single molecule, a phenomenon that is only possible under conditions of very high laser power and tight beam focusing. For this reason, multiphoton excitation occurs only in a small volume around the focal point of the irradiating laser, while chromophores elsewhere in the laser path are exposed only to isolated low-energy photons. The three-dimensional control of excitation provided by this technique has made it very useful in micro-lithography, in which objects (including photonic devices) with very small feature sizes can be made by the photo-initiated cross-linking of oligomers in resin form.[3] Recently, the formation of solid structures by multiphoton-induced cross-linking of soluble proteins in aqueous media has also been described.[4,5]

The photochemical patterning of agarose hydrogels covalently modified with S-2-nitrobenzylcysteine has been previously reported[6]. The photochemical patterning of hyaluronan hydrogels covalently modified with S-2-nitrobenzylcysteine has also been described in a publication co-authored by one of the present inventors[7] (the subject matter of these publications is incorporated by reference into the present application). Irradiation of these hydrogels with a conventional ultraviolet (UV) laser removed 2-nitrobenzyl protecting groups along the path of the laser beam, providing cylindrical volumes of free thiols through the full thickness of the hydrogel samples. Treating the patterned gels with maleimide-modified oligopeptides then resulted in the covalent immobilization of these molecules in the irradiated volumes via Michael-type addition, providing bulk substrates with cell-adhesive, cylindrical volumes defined in a purely chemical fashion (i.e., without altering the local mechanical properties).

6-bromo-7-hydroxycoumarin (Bhc) chromophore[8] is well-attested as an efficient, multiphoton-labile ($\delta_u$~1 GM at 740 nm) protecting group for amines[8], alcohols and phenols[9], aldehydes[10], and diols,[11,12] and has also been used extensively as a phototrigger inside biological systems.[8,13]

SUMMARY

In one aspect, the present invention provides a modified hydrogel comprising: a hydrogel modified by a multiphoton photocleavable molecule bound thereto, the molecule comprising a multiphoton-labile protective group and a protected group, wherein the protective group is cleavable upon multiphoton excitation to deprotect the protected group, without substantial polymerization of the hydrogel.

In another aspect, the present invention provides a chemically patterned modified hydrogel comprising the modified hydrogel according to the invention wherein a portion thereof comprises groups deprotected by exposure to multiphoton excitation.

In yet another aspect, the present invention provides a method of preparing a modified hydrogel comprising: conjugating a multiphoton photocleavable molecule having a multi-photon labile protective group and a protected group to a hydrogel, wherein the protective group is cleavable upon multiphoton excitation to deprotect the protected group, without substantial polymerization of the hydrogel. In one embodiment, the method further includes the step of preparing the multiphoton photocleavable molecule.

In yet another aspect, the present invention provides a method of chemically patterning a modified hydrogel of the present invention comprising irradiating the modified hydrogel with a light of sufficient intensity to deprotect a portion of the protected groups. In one embodiment, chemically patterned hydrogels of the present invention are exposed to bioactive molecules and are useful for cell guidance applications. In another embodiment, chemically patterned hydrogels of the present invention are useful for drug delivery.

In yet another aspect, the present invention provides a multiphoton photocleavable molecule consisting of 4-((2-aminoethylthio)methyl)-6-bromo-7-hydroxy-2H-chromen-2-one.

BRIEF DESCRIPTION OF THE DRAWINGS

The file of this patent contains at least one drawing/photograph executed in color. Copies of this patent with color drawings will be provided by the Office upon request and payment of the necessary fee.

The present invention will be described with reference to the following drawings wherein like reference numerals indicate like parts and in which.

DETAILED DESCRIPTION OF ILLUSTRATIVE ASPECTS

Figure 1:
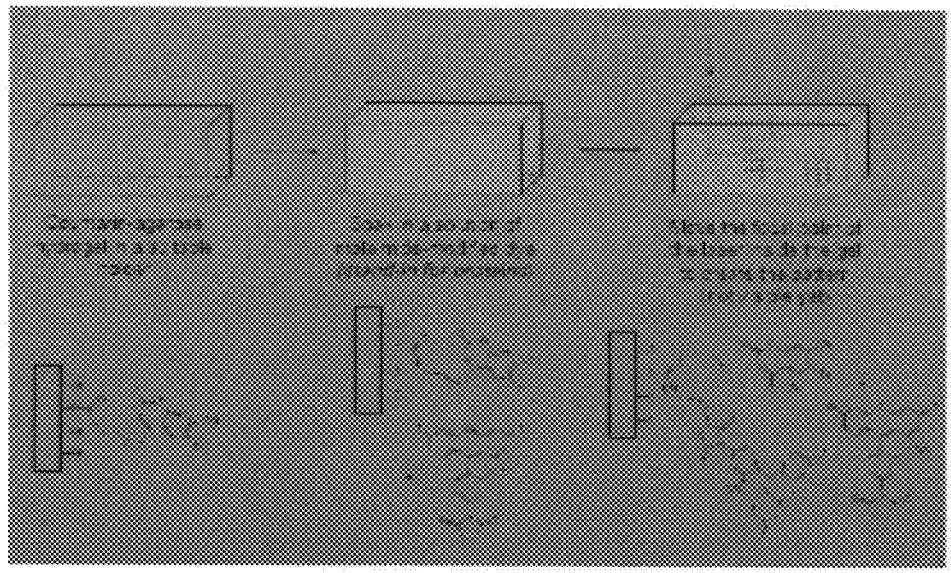
FIG. 1 illustrates schematically a method of patterning a modified hydrogel in accordance with the present invention.

The present invention involves use of multiphoton excitation as a tool for creating three-dimensional, functional group-based modifications inside gels, without using the more conventional photo-initiated gel cross-linking[14] or otherwise changing the physical or mechanical properties of the materials being patterned, to form what is termed herein a "chemically patterned hydrogel". The present invention is particularly useful in that it permits the formation of repeated, complex chemical patterns inside hydrogel samples. Among other uses, hydrogels of the present invention are useful in cell guidance and tissue engineering. For example, 2-nitrobenzyl-cysteine-modified agarose hydrogels can be used to immobilize a fibronectin-based peptide, GRGDS, capable of promoting integrin-mediated neural cell adhesion, to specific photoactivated sites within the modified hydrogel in order to enable neural cell localization, migration and cell process extension, indicative of the guidance effect of the chemical pattern within the hydrogel.

As explained above, multiphoton excitation or absorption is the near simultaneous absorption of two or more photons to reach a reactive, excited state that is energetically inaccessible by the absorption of a single photon of the same energy.

A chemically patterned hydrogel of the present invention is formed via conjugation of a hydrogel with a multi-photon photocleavable molecule to form a modified hydrogel, followed by focussed cleavage of the multi-photon photocleavable molecule.

While the hydrogel used in the present invention is not particularly restricted and its selection is within the purview of a person skilled in the art, the hydrogel may suitably be selected from: a polysaccharide, a protein-based gel, a peptide-based gel or a synthetic gel. Suitably, the hydrogel is a hyaluoronan gel, an alginate gel, a polyethylene glycol (PEG)-based gel or dextran-based gel. Most suitably, the hydrogel is an agarose gel.

The multiphoton photocleavable molecule used in the present invention has a multiphoton-labile protective group and a protected group. The protective group is cleavable upon multiphoton excitation to deprotect the protected group, without substantial polymerization or crosslinking of the hydrogel.

The multiphoton photocleavable molecule may be selected from a coumarin-protected molecule, a 2-nitrobenzyl-protected molecule, a 7-nitroindoline-protected molecule, and a p-hydroxyphenacyl-protected molecule. In one embodiment, the multiphoton-labile protective group is a coumarin and, suitably, the coumarin-protected group is a sulphide. In an alternate embodiment, the coumarin-protected group is an amine. Other protected groups include: alcohols, phenols, carboxylates, sulfates, phosphates, aldehydes, ketones and diols.

In one embodiment, the multi-photon photocleavable molecule is a sulphide derivative of 6-bromo-7-hydroxycoumarin ("Bhc"): 4-((2-aminoethylthio)methyl)-6-bromo-7-hydroxy-2H-chromen-2-one. This 6-bromo-7-hydroxycoumarin sulfide (3) can be conjugated to an agarose gel as shown in Scheme 1 and as described in more detail in Example 1.

Scheme 1. Synthesis of coumarin-derivatized agarose 4 (0.2% degree of substitution - coumarin moities are indicated on the polymer repeat structure for clarity).

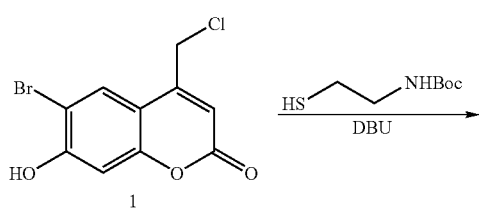

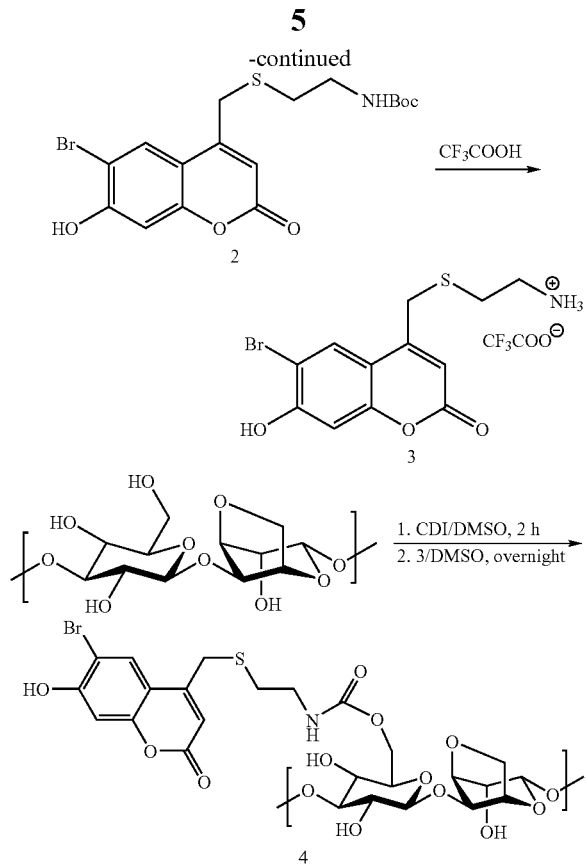

In another embodiment, the multi-photon photocleavable molecule is an amine derivative of 6-bromo-7-hydroxycoumarin ("Bhc"): 6-bromo-7-hydroxy-2-oxo-2H-chromen-4-yl(methyl 2-aminoethylcarbamate).

The light source used for multiphoton excitation is not particularly restricted and its selection is generally within the purview of a person skilled in the art. Generally, any light source that provides sufficient intensity (to effect multiphoton excitation) at a wavelength appropriate for absorption by the multiphoton-labile protective group may be used. Suitable light sources include UV light or a pulsed infrared light. Suitable wavelengths of light can generally be between 200 nm and 1500 nm; 600 nm to 900 nm; and preferably 710 nm to 800 nm. For the Bhc embodiment, suitable ranges are generally 200 nm to 450 nm when UV light is used for irradiation, preferably 325 nm to 400 nm; and 710 nm to 900 nm when pulsed IR irradiation is used, preferably 700 nm to 750 nm. Suitably, a Ti/sapphire multi-photon confocal laser is used to photocleave the coumarin group at specific focal points. While determination of the optimal rastering rate will be within the purview of persons skilled in the art, the optimal rastering rate for a rasterized pulsed IR laser has been found to be 0.01-0.03 mm$^2$/s, which corresponds to 33-100 s/mm$^2$ of the patterned area, or 0.03-0.1 ms/μm$^2$. Such rastering rates are achieved with rasterization and not upon bulk exposure.

Photocleavage suitably leaves deprotected groups capable of further modification. In one embodiment, the deprotected group is a thiol and a further modification is by way of Michael-type addition, a SN2 displacement reaction, or a disulfide bond formation. In another embodiment, a further modification occurs by reaction between the thiol group and a molecule bearing an unsaturated imide group; in one embodiment, the unsaturated imide group is maleimide. In another embodiment, the deprotected group is an amine functional group and a further modification is via reaction with molecules capable of reaction with amine functional groups, including activated carboxylic acids, carboxylic acids, esters, aldehydes, acyl chlorides, hydroxyls and activated hydroxyls.

In one embodiment, covalent modification of agarose with a 6-bromo-7-hydroxycoumarin (Bhc) sulfide derivative yields a hydrogel that generates bound thiol groups upon excitation with either UV light or a pulsed infrared laser. Using a multiphoton confocal microscope as the patterning platform, chemically modified volumes of stable nucleophilic thiol groups can be created inside these hydrogel samples, which in turn can be modified, e.g. with biomolecules or fluorescent dyes, without causing hydrogel crosslinking or changes in its physical properties. Evidence that there is no substantial cross-linking is demonstrated by the fact that the subsequent modifications may be temporally spaced from the irradiation of the gel with multiphoton excitation, indicating that the system remains sufficiently fluid to permit migration and reaction of the modifying molecules.

In one embodiment, after photoactivation, the patterned hydrogel is exposed to bioactive molecules having functional groups capable of reacting with the activated multi-photon photocleavable group. Suitable bioactive molecules are not particularly restricted and are within the purview of persons skilled in the art. Suitable bioactive molecules include proteins, peptides, polysaccharides, drugs, growth factors, hormones, vitamins, enzymes, genes and small molecules. In one embodiment, the bioactive molecule stimulates one or more of cell adhesion, cell differentiation and cell growth. In one embodiment, the bioactive molecule is selected from biotin, laminin, collagen, fibronectin, peptide mimetics, the synthetic peptide RGD (derived from fibronectin or laminin), RGD derivatives, the synthetic peptide YIGSR (derived from laminin), YIGSR derivatives, the synthetic peptide IKVAV (derived from laminin), IKVAV derivatives, growth factors and small molecules capable of differentiating stem cells. Suitable bioactive molecules are within the purview of persons skilled in the art and may be commercially available or easily synthesized.

Figure 2:
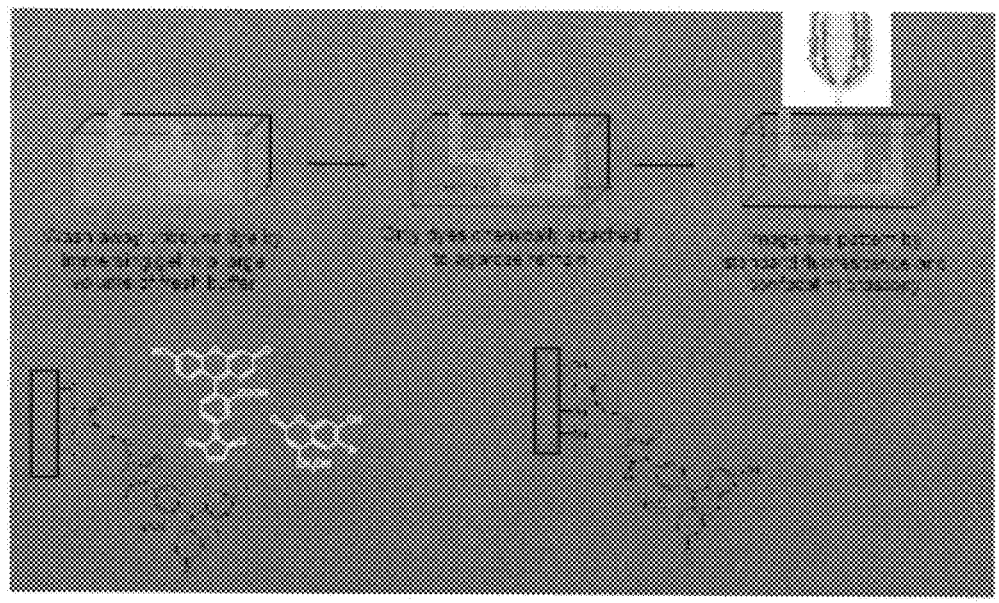
FIG. 2 illustrates schematically a method of visualizing the patterning of a modified hydrogel in accordance with the present invention.

A method of patterning according to the invention is illustrated schematically in FIG. 1. In this example, a coumarin-agarose hydrogel of the present invention is provided as described above. In order to permit visualization of the patterning (shown schematically in FIG. 2), the hydrogel is soaked in a solution of biomolecules bound to dye, suitably a maleimide-modified dye. As will be apparent to persons skilled in the art, visualization of the pattern is an optional step and, for example, may be unnecessary where the patterning process is a repetition of a previously produced pattern. The focal point of the laser is then moved inside the gel to create the pattern. As will be apparent, the focal point may be moved by moving the laser or by moving the hydrogel. The addition of the biomolecule bound to dye can alternatively take place after the step of photoexcitation. The gel is then washed to remove dye-bound biomolecules not taken up by the modified hydrogel. The pattern can then be viewed by standard fluorescence and confocal microscopy.

Figure 3:
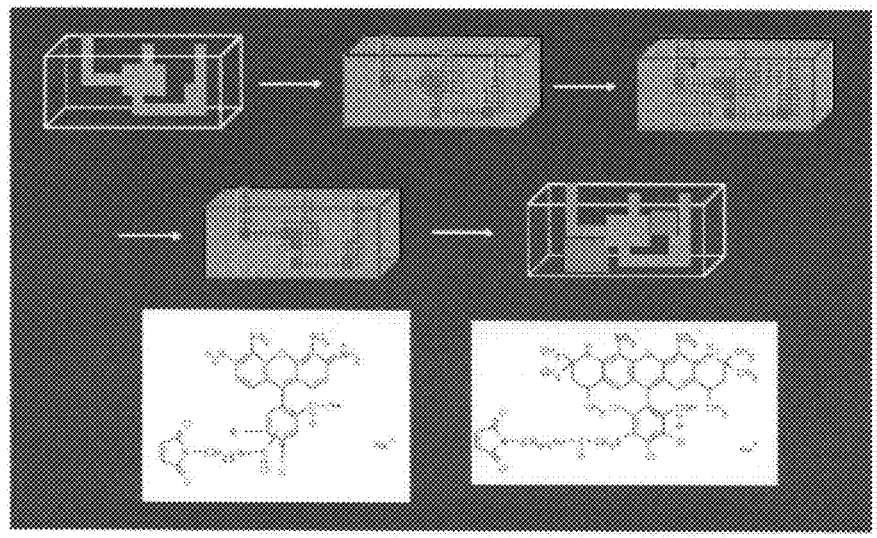
FIG. 3 illustrates schematically a method of patterning and visualizing a second-colour pattern alongside an existing colour pattern in a modified hydrogel of the present invention, where the colour represents a molecule of interest.

It is further possible to visualize second-colour patterning alongside existing patterns, as illustrated in an exemplary embodiment shown in FIG. 3. Visualization by means of dyes illustrates the patterning of bioactive molecules available i.e. the pattern represents the distribution of bioactive molecules, which do not have to be bound to a dye. The use of automated scripts and microscope stage control allows molecules of interest to be photochemically immobilized within the hydrogel in complex patterns, which may have feature sizes comparable to those of mammalian cells. While the preparation of suitable control scripts may be within the purview of persons skilled in the art and may be commercially available, in one embodiment, the invention includes those scripts that form part of the present description (see Appendix below). While applications for the present hydrogels are not particularly restricted, the resulting chemically patterned hydrogels have applications in tissue engineering, where they can be used to control cell behavior.

Accordingly, the patterned hydrogels of the present invention can be used as scaffolds for the adhesion, growth and differentiation of cells. The resulting three-dimensional functional-group patterns can be used as handles for the spatially defined introduction of bioactive molecules into the gels, which can in turn be used to simulate the patterned biochemical cues that are found in natural tissue. Suitably, these cells are mammalian stem cells and progenitor cells, including precursor cells. The source of these cells is not particularly restricted and their selection is within the purview of a person skilled in the art; however, suitably and without being limited thereto, the cells are derived from mammalian embryonic or adult cells derived from the brain, retina, mesenchyme, the hematopoetic system, cardiac tissue, skin, bone, nervous system, cartilage, vasculature and umbilical cord blood.

In this regard, the inventors have previously demonstrated that channels of GRGDS in agarose guide neurite extension of chick dorsal root ganglia (DRGs). A key factor in tissue engineering and repair is the ability to control growth and movement of cells. It has been demonstrated that the ability to immobilize a fibronectin-derived GRGDS peptide in a specific pattern within a hydrogel using UV light irradiation can provide a template for biomolecule immobilization 6a. These patterns are able to promote and guide the neurite extension of chick DRGs. Similar results have been achieved using coumarin-modified agarose. The coumarin-modified agarose was bulk irradiated to immobilize maleimide-GRGDS peptides throughout the hydrogel. Chick DRGs were plated on top of the hydrogel, and it was observed that the neurites were able to penetrate into the hydrogel. These earlier studies demonstrate the utility of the chemically patterned hydrogels of the present invention for cell and tissue growth and development applications.

In another example demonstrating the utility of the hydrogels in cell guidance and tissue engineering, 2-nitrobenzyl-cysteine-modified agarose hydrogels can be used to immobilize a fibronectin-based peptide, GRGDS, capable of promoting integrin-mediated neural cell adhesion, to specific photoactivated sites within the modified hydrogel in order to enable neural cell localization, migration and cell process extension, indicative of the guidance effect of the photoactivation induced chemical patterning within the hydrogel.

The present invention finds application in tissue engineering, including tissue replacement, tissue repair and tissue regeneration, including, without limitation, tissue engineering of retina, brain cortex, blood vessels, and cardiac patches.

The present invention also finds application in drug delivery. Suitably, modified hydrogels of the present invention can have drugs distributed/bound within different regions of the hydrogels to mediate the time and rate of release of the drug. In one application, for example, a drug or drugs attached to the exterior of the hydrogel would be released earlier and a drug or drugs attached in the center of the hydrogel would be released later. As will be apparent to a person of skill in the art, the exterior and interior drugs may be the same or may be different and a modified hydrogel of the invention could be used to deliver multiple drugs.

The present invention also finds application in use of the modified hydrogels to immobilize biomolecules via a degradable linker to enable localized cells to actively take up the biomolecule upon entering the microenvironment. As an example, the degradable linker could be a hydrolysable linker or an enzyme-susceptible linker.

The following Exemplary Aspects of specific examples for carrying out the present invention are offered for illustrative purposes only, and are not intended to limit the scope of the present invention in any way.

EXEMPLARY ASPECTS

Example 1

Synthesis of Coumarin-Derivatized Agarose with Thiol Protected Group

A coumarin-derivatized agarose of the present invention was prepared according to Scheme 1 below.

Scheme 1. Synthesis of coumarin-derivatized agarose 4 (0.2% degree of substitution—coumarin moieties are indicated on the polymer repeat structure for clarity). The sulfide-containing amine 3 $\lambda_{max}$=373 nm, $\epsilon$=14,500 $M^{-1}$ $cm^{-1}$ in 0.1 M HEPES, pH 7) was prepared in two steps from the previously reported chloride derivative 1 and commercially available Boc-protected mercaptoethylamine. Conjugation of 3 to agarose was carried out in dimethylsulphoxide (DMSO) using 1,1-carbonyldiimidazole (CDI)[6]. Following dialysis and freeze-drying, derivatized agarose 4 was obtained in good yield with ca. 0.2% substitution (based on moles of 3 per agarose repeat unit).

All nuclear magnetic resonance (NMR) spectra were collected on a Varian Mercury 400 spectrometer and are referenced to the resonances of residual protonated solvents (for acetone-$d_6$: $^1$H resonance at 2.05 ppm, $^{13}$C resonance at 29.9 ppm). Mass spectra were recorded on an AB/Sciex QStar mass spectrometer with ESI source. Infrared (IR) spectra were measured on a Nicolet Avatar 370 MCT Fourier transform-(FT)-IR spectrophotometer. All chemicals were purchased from Sigma-Aldrich and used as received unless otherwise specified.

Synthesis of 2: A solution of compound $1^8$ (1.33 g, 4.6 mmol), 1,8-diazabicyclo[5.4.0]undec-7-ene (DBU) (800 ml), and N-(tert-butoxycarbonyl)-aminoethanethiol (0.88 ml, 5.2 mmol) in tetrahydrofuran (THF) (50 ml) were heated at reflux overnight in the dark under a nitrogen atmosphere. After cooling to room temperature, the reaction mixture was evaporated to dryness, taken up in ethyl acetate (EtOAc) and washed with dilute aqueous hydrochloric acid (HCl) and brine. The organic phase was separated, dried over anhydrous magnesium sulfate ($MgSO_4$) and evaporated to an orange-colored oil which was

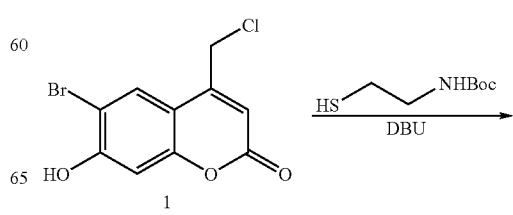

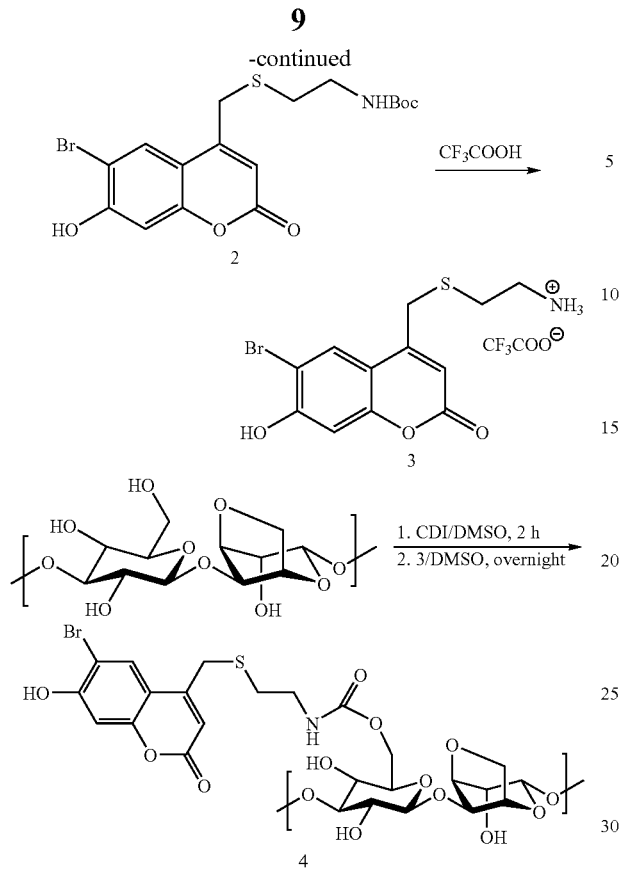

chromatographed on silica gel (6% MeOH in $CH_2Cl_2$) to provide a clear, viscous oil, which solidified on standing (yield 1.00 g, 52%). Proton ($^1H$) NMR (acetone-$d_6$, ppm): 1.40 (s, 9H), 2.68 (t, 2H, J=6.8 Hz), 3.31 (m, 2H), 3.99 (s, 2H), 6.16 (br s, 1H), 6.33 (s, 1H), 6.92 (s, 1H), 8.04 (s, 1H), 9.99 (s, 1H). $^{13}C$ NMR (acetone-$d_6$, ppm): 28.7, 32.1, 32.4, 40.6, 104.6, 106.7, 113.3, 130.6, 151.9, 155.9, 157.9. HRMS: calcd for $[C_{17}H_{20}NO_5SBrNa]$ 452.0137, found 452.0149.

Synthesis of 3: A solution of 2 (780 mg, 1.8 mmol) in methylene chloride ($CH_2Cl_2$) (10 ml) was treated with trifluoroacetic acid ($CF_3COOH$) (1 ml) and the reaction mixture stirred in the dark for 4 hours (here forwarded denoted as "h"). The reaction mixture was evaporated to dryness, re-suspended in water, and lyophilized, to provide an off-white powder in quantitative yield, pure enough for further use. Analytically pure samples were obtained by preparative reverse-phase high pressure liquid chromatography (HPLC) ($C_{18}$ column, 10/90 to 90/10 $MeCN/H_2O$ gradient over 80 mins with constant 0.1% TFA). $^1H$ NMR (acetone-$d_6$, ppm): 3.10 (t, 2H, J=7.6 Hz), 4.09 (t, 2H, J=7.0 Hz), 4.09 (s, 2H), 6.37 (s, 1H), 7.01 (s, 1H), 8.00 (s, 1H). $^{13}C$ NMR (acetone-$d_6$, ppm): 32.4, 47.7, 104.6, 106.7, 113.2, 130.4, 151.8, 155.9, 158.3, 160.4, 168.0. FT-IR (KBr pellet, $cm^{-1}$): 3420, 3087, 1709, 1604, 1382, 1270, 1203, 875, 850, 722. UV-Vis: ($\lambda_{max}$=375 nm ($\epsilon$=14,600 $M^{-1}cm^{-1}$) in 0.1 M HEPES, pH 7.0. HRMS: calcd for $[C_{12}H_{12}NO_3SBr.H]$ 329.9794, found 329.9808.

Preparation of 4: Type IX agarose (Ultra-low gelling temperature, Sigma) (0.80 g) was dissolved in 40 ml of hot DMSO. After cooling to room temperature, 1,1-carbonyldiimidazole (0.36 g) in 4 ml DMSO was added, and the reaction mixture was stirred under nitrogen for 2 h. Coumarin 3 in DMSO (60 mg in 1 ml) was then added dropwise, followed by 5 drops of triethylamine ($Et_3N$), and the solution was stirred overnight under nitrogen. After dilution to ca. 200 ml with water, the agarose solution was dialyzed against deionized water for 5 days (here forward denoted as "d") in the dark, with frequent water changes. The solution remaining after dialysis was lyophilized in the dark to yield a spongy, white fluorescent solid ($\lambda_{abs}$=375 nm). The degree of substitution was determined to be 0.2% based on $A_{375}$ values for solutions of 4 of known concentration.

Example 2

Verifying Ability of Hydrogels to Form Agarose-Bound Thiols on Irradiation

Figure 4:
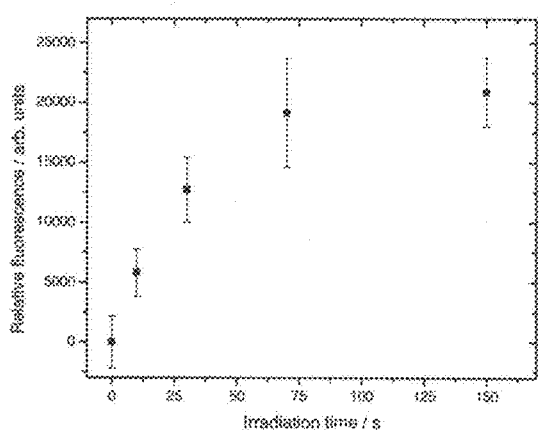
FIG. 4 illustrates in graph representation the extent of fluorescein-5-maleimide immobilization in a modified hydrogel of the present invention (4 in Scheme 1) following irradiation as a function of irradiation exposure time (Mean±standard deviation, n=4)

To verify the ability of hydrogels of 4 to form agarose-bound thiols on irradiation, solutions of 4 (1.25% in HEPES buffer, pH 7.0) were irradiated with ultraviolet (UV) light (350 nm) for various time intervals. Aliquots of the irradiated solution were removed, mixed with excess fluorescein-5-maleimide (a thiol-reactive fluorescent dye), cooled at 4° C. for 2 h to induce gelation, and washed extensively with buffer. Emission from the immobilized fluorescein groups in the resulting gels was found to increase with irradiation time (FIG. 4), clearly demonstrating a light-dependent immobilization process.

Example 3

Multiphoton Chemical Pattern Writing in Hydrogels

Figure 5:
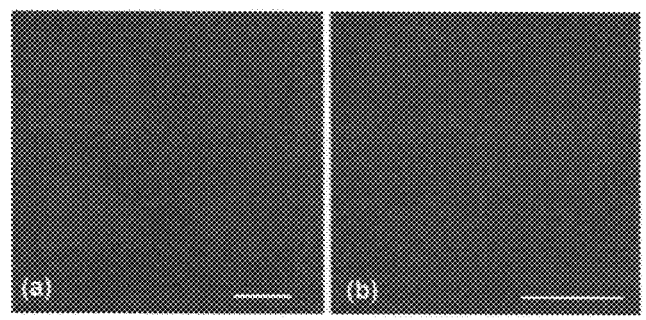
FIG. 5 illustrates confocal micrographs of fluorescent (a) geometric shapes and (b) a grid, created by photochemical immobilization of AF488-Mal in a modified hydrogel sample of the present invention (4 in Scheme 1) using multiphoton irradiation guided by software-delineated regions of interest. Scale bars are 50 μm.

Multiphoton chemical pattern writing in hydrogels of 4 was tested by irradiating hydrogel samples (1% in 0.1 M PBS, pH 7.4) with a commercial Ti-Sapphire femtosecond laser (Spectra Physics Mai Tai) in the presence of a thiol-reactive fluorescent dye (0.5 mg/ml Alexa Fluor 488 Maleimide [AF488-Mal], Invitrogen). Gels were placed on the sample stage of a commercial confocal microscope (Leica TPS SP2) and the microscope control software was used to delineate geometric "regions of interest" (ROIs) for raster-scanning of the laser focal point within a plane set to any desired depth below the surface of the gel. After irradiation, hydrogels were washed exhaustively to remove non-immobilized dye, revealing sharp-edged fluorescent areas corresponding to the patterned ROIs (FIG. 5). It was found that a single scan at the maximum available laser power (100 mW average at 740 nm) was sufficient for the creation of clear patterns following washing.

3D Hydrogel Patterning and Visualization Procedures:

In a typical experiment, a solution of 4 (0.1% in hot 0.1 M PBS) containing 0.5 mg/ml Alexa Fluor 488 $C_5$ maleimide (AF488-Mal) (Invitrogen) was pipetted into a shallow, open container with a glass bottom (small rubber "O-rings" glued onto microscope cover slips are convenient for this purpose). After cooling in a refrigerator for ~2 h to ensure complete gelation, gel samples were mounted on the stage of a Leica TPS SP2 confocal microscope equipped with a Leica 20×/0.5 HC PL Fluotar objective lens and a Spectra-Physics Mai Tai broadband Ti-Sapphire laser, tuned to 740 nm. After focusing the laser to a plane in the interior of a gel at low power, the Leica software was used to define a "region of interest" (ROI), the laser power was increased through software controls to the maximum available (~100 mW average power), and a single scan was performed at a scan rate of 400 Hz (corresponding to 0.01-0.03 $mm^2/S$, depending on the size of the ROI). 2D arrays and 3D volumes were built up by automatically incrementing stage positions between scans, using microscope control scripts written in-house using the Leica/

Visual Basic software interface. After patterning, gel samples were immersed in buffer and gently agitated for several hours (for small gels) or days (for thicker gels) to remove reaction byproducts and unbound dye. Gels were then imaged by epifluorescence or standard confocal techniques.

Measurement of axial "thickness" of patterned regions: A pattern created by the procedure described above was imaged in the z-stack mode of the Leica TPS SP2 confocal microscope using standard techniques. A plot of AF488 fluorescence vs. z-position was fit to a Gaussian distribution with standard deviation $\sigma$=4.4 μm. Based on the statistical principle that approximately 95% of the area underneath a Gaussian distribution lies within $2\sigma$ of the mean, it can be concluded that 95% of the immobilized AF488 lies within a region of thickness $4\sigma$, or approximately 18 μm.

Example 4

Specificity and Mechanism of Immobilization in Hydrogels

The specificity and mechanism of immobilization in hydrogels of 4 was examined by attempting multiphoton laser patterning under a variety of conditions. Pattern formation was found to be efficient at laser wavelengths in the 710-800 nm range, consistent with the two-photon action profile expected for 3, which has an estimated maximal two-photon excitation around 740-750 nm ($\approx\lambda_{max}$). Additionally, in contrast to multiphoton gel patterning methods that rely on radical crosslinking,[8] laser-patterning of hydrogels of 4 can be and was performed several hours prior to the introduction of AF488-Mal without noticeable changes in the efficiency of dye immobilization. This result suggests the formation of agarose-bound thiols that remain reactive for prolonged periods and provides a means for the direct photopatterning of maleimide-modified molecules that are themselves photosensitive. To test the specificity of the chemical reaction between multiphoton-generated agarose-thiols and maleimide-modified fluorescent molecules, patterns were written in hydrogels of 4 containing equal concentrations of sulforhodamine 101, tetramethylrhodamine cadaverine, and AF488-Mal. After washing, these hydrogels yielded patterns consisting only of the maleimide-modified AF488 fluorophore, as determined by confocal fluorimetry. The formation of active thiol intermediates was confirmed by treating irradiated hydrogels with a large excess of 3-maleimidopropanoic acid prior to the introduction of AF488-Mal, a process that prevented fluorescent pattern formation due to the rapid reaction of thiol groups with the non-fluorescent maleimide derivative. Moreover, the presence of the covalently-bound Bhc-sulfide unit was necessary for pattern formation: patterning plain agarose hydrogels in the presence of soluble 3 and AF488-Mal did not yield visible patterns after washing.

Example 5

Figure 6:
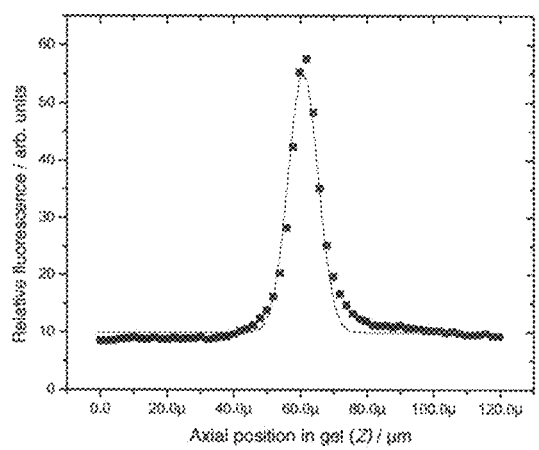
FIG. 6 illustrates axial distribution of immobilized AF488-Mal (black squares) after a single multi-photon patterning scan within a sample of a modified hydrogel of the present invention (4 in Scheme 1), followed by washing. The red line represents a Gaussian fit with σ=4.4 μm.

Evaluation of Degree of Three-Dimensional Control Available in Multiphoton Chemical Patterning of Hydrogels The degree of three-dimensional control available in multiphoton chemical patterning of hydrogels of 4 was evaluated by measuring the axial distribution of immobilized AF488-Mal in patterned volumes (such as those illustrated in FIG. 5) using confocal microscopy. After patterning within a single focal plane, the dye concentration along the z-axis—a measure of the probability of excitation of coumarin moieties during patterning—was found to assume a Gaussian distribution, as expected from optical considerations (FIG. 6)[15] The width of these distributions in hydrogels of 4 typically showed a standard deviation $\sigma$=4.4 μm, indicating that $\approx$95% of the immobilized molecules lie within 9 μm of the focal plane selected during patterning. The resulting chemical patterns thus had total thicknesses of ca. 18 μm ($4\sigma$), which is comparable to the size of a single mammalian cell. This figure was somewhat larger than what would be expected based on microscope resolution alone, likely due to thermal motion of agarose chains during and after irradiation. [The size of the axial distribution of two-photon excitation about the focal point is proportional to $1/NA^2$, where NA is the numerical aperture of the objective used. While the thickness of the patterns in the system of the present invention can be narrowed by patterning gels with a lens of higher NA, the objective used for this study (Leica 20×/0.5 HC PL Fluotar) was selected as a compromise between axial resolution and working distance, which is inversely related to NA.

Figure 7:
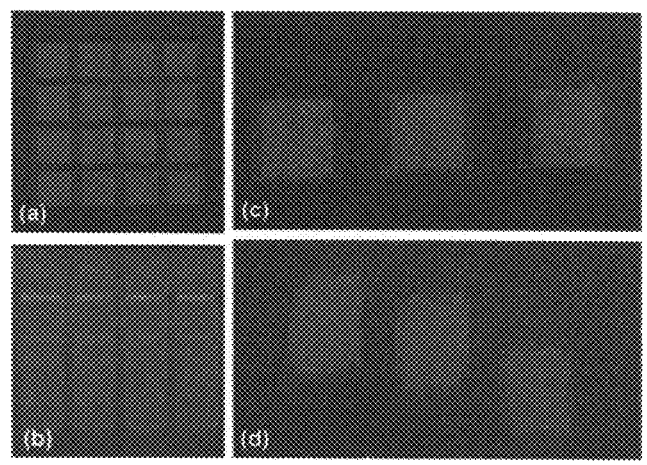
FIG. 7 illustrates (a) top and (b) side views of a 4×4×4 array of patterned squares (60 μm per side) of AF488-Mal with 50-μm inter-layer spacing. (c) top and (d) side views of continuous volumes (ca. 150 μm in height) of AF488-Mal modified hydrogel created by stacking 100×100×18 μm patterned squares at small z-spacing increments.
Figure 8:
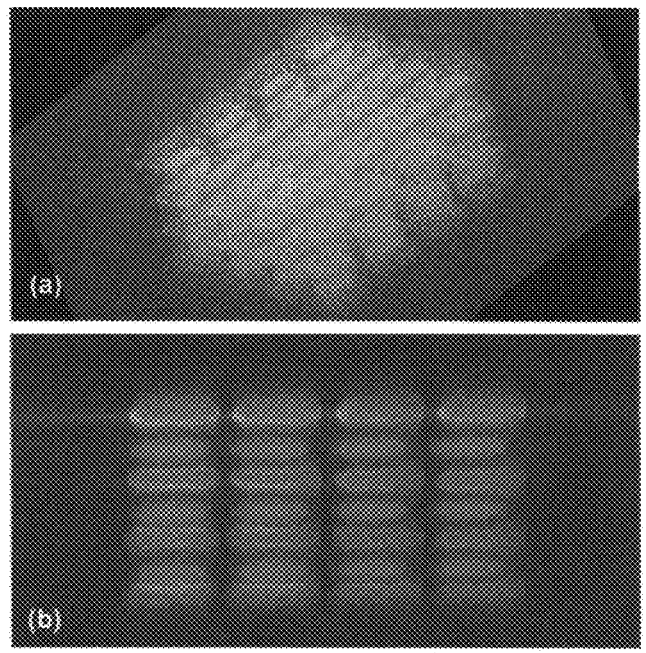
FIG. 8 illustrates (a) oblique and (b) side views of the 4×4×4 array of 3D patterned squares from FIG. 7a-b, overpatterned with a second 4×4×3 array of circles (ca. 50 μm diameter) of the red fluorescent dye AF546-Mal.

The relatively thin nature of individual patterned volumes was exploited to create fully three-dimensional patterns by controlling the spacing between adjacent shapes. The hardware scripting function of the Leica TPS SP2 microscope was used to write programs that automated the formation of arrays of flat shapes (such as the 4×4×4 array of flat squares shown in FIGS. 5a and b) by changing the stage position according to user-selected values. Continuous 'solid' shapes of immobilized dye, such as cubes (FIGS. 7c and d), could similarly be created by reducing the inter-layer spacing below 18 μm and using custom hardware scripts to control xyz stage motion. In addition, previously patterned gels of 4 were subjected to an additional patterning cycle using the red-fluorescent Alexa Fluor 546 Maleimide (AF546-Mal) to create 'two-color' patterns, derived from two distinct patterned molecules, with excellent three-dimensional precision (FIG. 8).

Example 6

Site-Selective Deposition of Biologically Relevant Molecules Inside Gels

Figure 9:
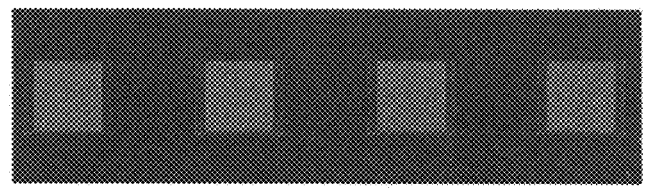
FIG. 9 illustrates squares (75 μm per side) formed by patterning a non-fluorescent, maleimide-modified biotin derivative approximately 200 μm below the surface of a modified hydrogel of the present invention (4 in Scheme 1), followed by blocking and staining the gel with AF546-labeled streptavidin.

Hydrogels of 4 (1% in PBS) containing maleimide-derivatized biotin (1 mg/ml Biotin-PEO$_2$-Maleimide, Pierce) were patterned using the techniques described above. After washing and blocking (1% BSA in PBS) the gel samples, a small quantity of AF546-labelled streptavidin was added to visualize the immobilized biotin. Confocal micrographs of the resulting patterns demonstrate the localization of the fluorophore-labelled streptavidin within areas containing immobilized biotin (FIG. 9).

Example 7

Synthesis of Derivatized-Coumarin with Hydroxyl Protected Group (Published Procedure)

Scheme 2.

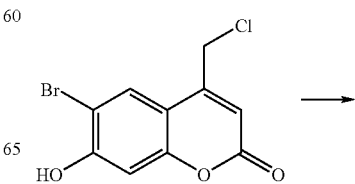

-continued

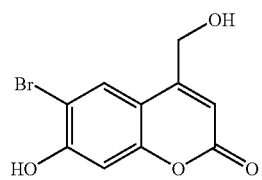

A mixture of 1 g of chlorocoumarin and 1.5 L of water was heated to reflux under magnetic stirring. Once the solid dissolves, the solution was cooled and concentrated to dryness. (100% yield)

Example 8

Synthesis of Coumarin-Derivatized Agarose with Amine Protected Group

Scheme 3. Preparation of Coumarin-NH₂Boc

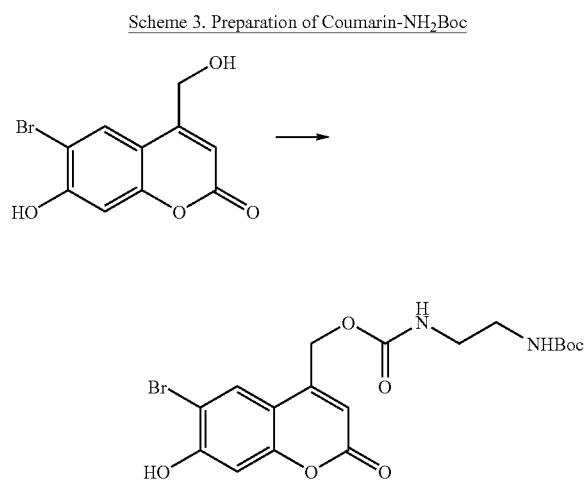

500 mg of the Coumarin-OH was dissolved in 100 ml of dichloromethane. Once dissolved CDI and dimethylaminopyridine (DMAP) were added. The mixture was stirred for 4 h at room temperature shielded from light. Mono-boc protected ethylene diamine was added to the solution and left to stir overnight at room temperature. The solution was diluted with dichloromethane and washed with 10% citric acid. The organic layer was then dried over magnesium sulphate and concentrated to dryness. The solid was purified by trituration in 20 ml of dichloromethane and dried yielding 240 mg of coumarin amine. (30% yield)

Scheme 4. Deprotection to Coumarin-NH₂

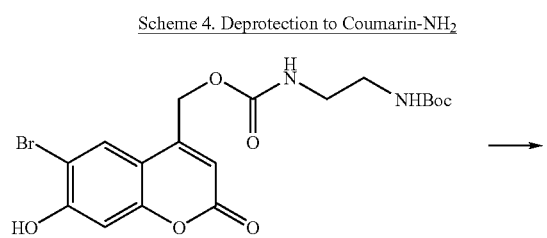

-continued

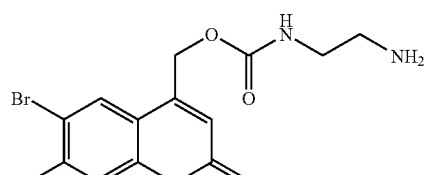

The solid was stirred in 9 ml of dichloromethane (DCM) and 1 ml of trifluoroacetic acid (TFA) for 4 h. The resulting solution was concentrated. (100% yield)

Scheme 5. Agarose-Coumarin (same procedure as thiol coumarin).

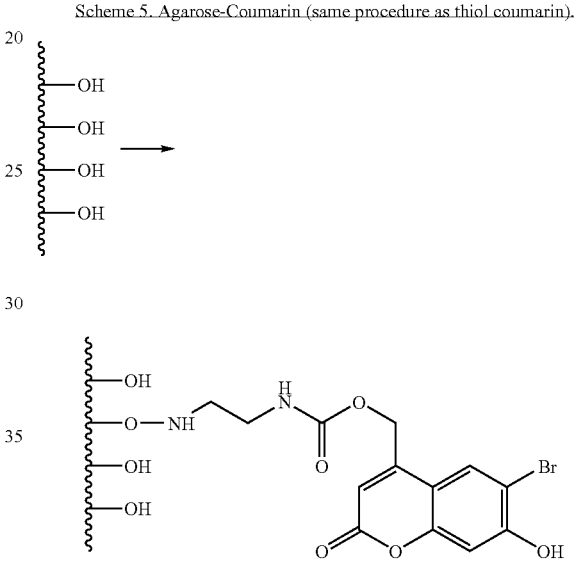

There were 0.0963 moles of aminocoumarin per mole of agarose monomer covalently immobilized, yielding a degree of substitution of 9.63%.

Agarose was first activated. 200 mg of Agarose was dissolved in 10 ml of DMSO. 50 mg CDI was added to the solution and stirred for 3 h. While being shielded from the light, 18 mg coumarin-NH₂ was added and left to stir overnight at room temperature. The solution was then purified by dialysis and freeze dried to give a white solid. (90% yield)

Scheme 6.
Photoactivation of coumarin-derivatized agarose with amine protected group

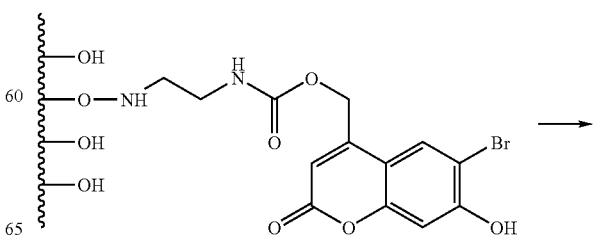

-continued

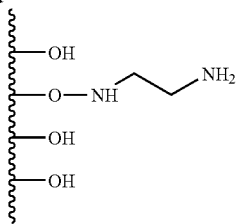

The presence of amine functional groups after photo-irradiation was confirmed by reaction with CBQCA, which is an amine-specific fluorescent label. The fluorescent intensity associated with CBQCA bound to amine-functionalized agarose was ca. 3500 relative fluorescence units (RFU's) which is significantly greater than the intensity associated with non-irradiated samples (and exposed to CBQCA), which was approximately 500 RFU's.

Figure 10:
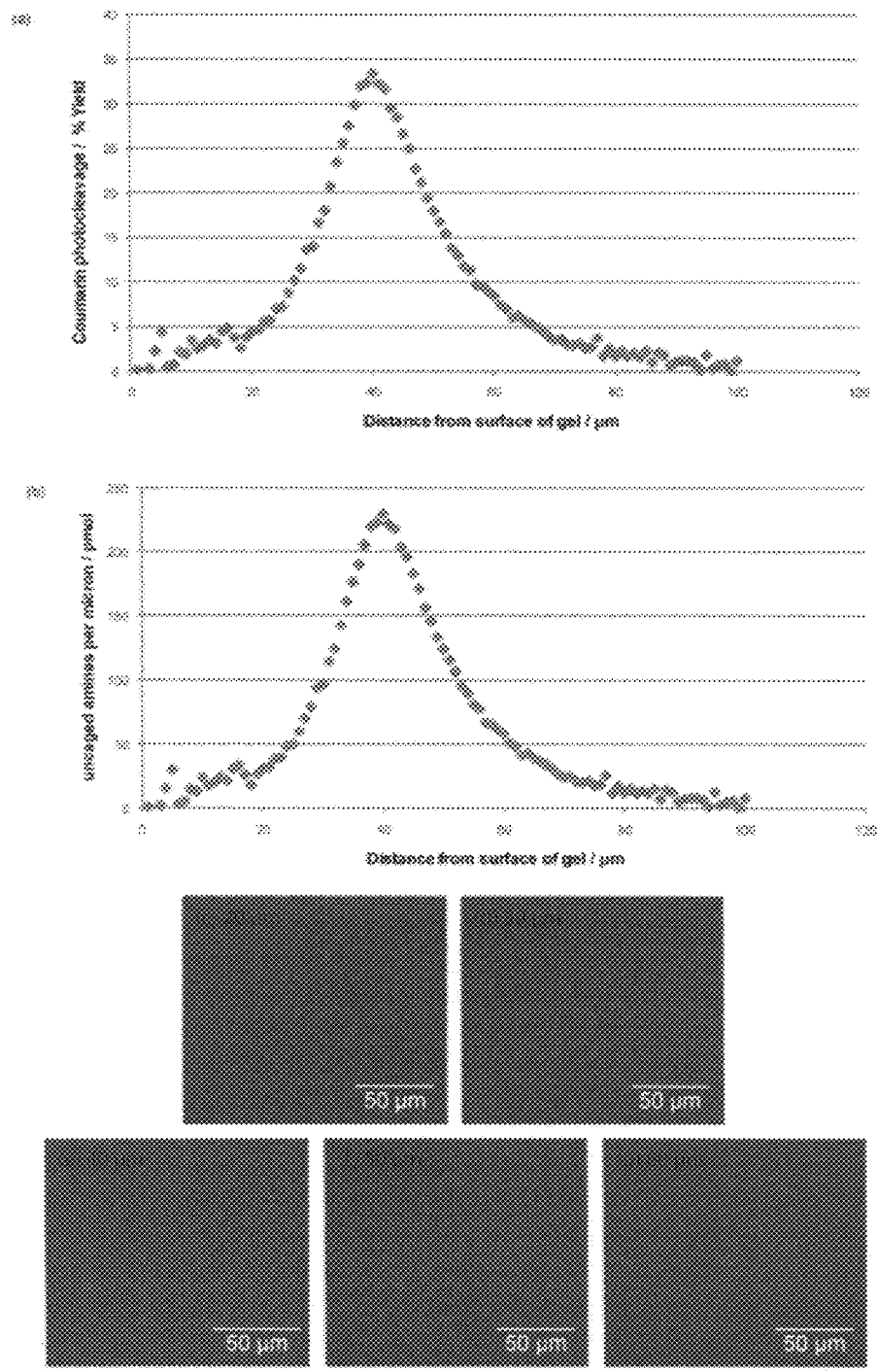
FIG. 10 illustrates a 50 by 50 μm box that was patterned 40 μm below the surface of the gel. The yield of reaction (percent of coumarin photocleavage and pmol of amines) was determined by measuring the decrease in coumarin fluorescence within the patterned region. The change in fluorescence intensity of coumarin was measured over the patterned region through the first 100 μm. The box was scanned three times with the pulsed Ti-Sapphire laser set to 740 nm. (a) The yield of coumarin deprotection by two-photon irradiation was then calculated as a function of depth by comparing the change in coumarin fluorescence in the patterned region to a non-patterned region. (b) The amount of amines in picomol as a function of depth within the patterned region. Confocal micrographs of coumarin fluorescence are shown at: (c) 20 μm, (d) 30 μm, (e) 40 μm, (f) 50 μm and (g) 60 μm below the surface.

As shown in FIG. 10, the yield of reaction (percent of coumarin photocleavage and pmol of amines) was determined by measuring the decrease in coumarin fluorescence within the patterned region. FIG. 10 illustrates a 50 by 50 μm box that was patterned 40 μm below the surface of the gel. The change in fluorescence intensity of coumarin was measured over the patterned region through the first 100 μm. The box was scanned three times with the pulsed Ti-Sapphire laser set to 740 nm. (a) The yield of coumarin deprotection by two-photon irradiation was then calculated as a function of depth by comparing the change in coumarin fluorescence in the patterned region to a non-patterned region. (b) The amount of amines in picomol as a function of depth within the patterned region. Confocal micrographs of coumarin fluorescence are shown at: (c) 20 μm, (d) 30 μm, (e) 40 μm, (f) 50 μm and (g) 60 μm below the surface.

Example 9

Neural Stem/Progenitor Cells (NSPCs) have been Shown to Survive in RGD Modified Agarose Typically, NSCs do not survive in non-modified agarose and RGD modification is crucial for cellular survival. Therefore, NSCs can be localized within an agarose hydrogel that is modified with the appropriate factors.

The survival of neural stem/progenitor cells was tested in an agarose hydrogel where a maleimide-modified glycine-arginine-glycine-aspartic acid-serine (GRGDS) peptide, a cell adhesion peptide, was attached. Survival was quantified using the MTT assay which detects metabolic activity. NSPCs did not survive in hydrogels having no attached peptide, but NSPCs in hydrogels having the peptide attached showed similar survival rates as in collagen controls. Therefore, agarose hydrogels chemically patterned with GRGDS proved to be a healthy environment for NSPCs.

These data show that chemically patterned hydrogels are suitable scaffolds for use in tissue engineering given the ability of these hydrogels to localize cells to specific regions.

Example 10

Two-Methods Used for the Immobilization of mal-GRGDS to Agarose

Two methods were used for the immobilization of mal-GRGDS to agarose: bulk and IR irradiation. In bulk irradiation the peptide is attached throughout the entire gel. Coumarin sulphide agarose was dissolved in PBS pH 7.4 (10 mg/ml), maleimide GRGDS (1 mg/ml) was then added and the solution was irradiated with a UV lamp for 2 min. The solution was incubated at 37° C. for 2 h. The unbound peptide was removed through dialysis against distilled water. The solution was then lyophilized to yield a white solid of agarose modified with GRGDS. Hydrogels can then be formed out of the GRGDS modified agarose as described in Example 1.

Example 11

Pattern Scripts

The scripting framework provided with the Leica TPS SP2 confocal microscope was used to generate scripts to control the motion of sample stage and the execution of patterning scans at user-controlled rates and intervals. These scripts provided an automated method for generating complex three-dimensional patterned regions within gels, such as grids, blocks, and helices with minimal operator intervention. These pattern scripts are included in the present application.

Example 12

Neural Stem/Progenitor Cells Will Differentiate in Response to Stimuli

Neural stem/progenitor cells will differentiate in response to stimuli, such as growth factors. Platelet-derived growth factor (specifically the AA homodimer, PDGF-AA) has been shown to promote differentiation to oligodendrocytes. PDGF-AA was immobilized in agarose gels by modifying PDGF-AA with a maleimide group (PDGF-AA-MI) and agarose with a photoprotected thiol group. Upon photoirradiation, agarose-SH reacts with PDGF-AA-MI, yielding covalently-bound agarose-PDGF-AA (via Michael addition of agarose-SH to PDGF-AA-MI).

Recombinant rat PDGF-AA was purchased from R&D Systems (Minneapolis, Minn., USA) and dissolved in 4 mM HCl with 10% 1,2-propanediol at a concentration of 400 μg/ml (40 μg/100 μl). The water-soluble carboimide, 1-ethyl-3-(3-dimethylaminopropyl) carboimide hydrochloride (EDC, 50 μl; Sigma-Aldrich) and N-Hydroxysulfosuccinimide (sulfo-NHS, 50 μl; Pierce) in 0.1 M 2-(N-morpholino) ethanesulfonic acid (MES) buffer, 1 M NaCl, pH 6 (reaction buffer) were added to the PDGF-AA solution to obtain a final concentration of 11 mM EDC and 12 mM sulfo-NHS. After mixing and reacting the above reagents at room temperature for 15 min, Alexa Fluor 350 hydrazide sodium salt (5 mM) in dimethyl sulfoxide (DMSO) and 4-(4-N-maleimidophenyl) butyric acid hydrazide (MPBH, 7 mM) in 0.1 M sodium acetate pH 5.5 (200 μl) were added to the PDGF-AA for 75 min at room temperature. After adding 20 mM HCl (80 μl), the modified PDGF-AA (MI-PDGF-AA) was purified with AKTA-FPLC (Amersham Pharmacia) using Sephadex G-25 (Sigma-Aldrich) column (10×200 mm) (Amersham Pharmacia) equilibrated in 4 mM HCl pH 2.3, 150 mM NaCl, 5% propanediol. Elution of MI-PDGF-AA was monitored at 280 nm using UV-Vis monitor (UPC-900 Pharmacia Biotech) equipped on the FPLC. Fluorescently tagged MI-PDGF-AA was confirmed by measuring fluorescent emission at 445 nm on a fluorescence plate reader (345 nm excitation, Molecular Device). The concentration of MI-PDGF-AA was determined using the PDGF-AA enzyme-linked immunosorbent assay (ELISA; R&D Systems). Assays were performed according to the manufacturer's instructions. The yield of MI-PDGF-AA was determined to be 30.4 μg (7.6 μg/ml), yielding 76% recovery. To confirm the conjugation of MPBH to PDGF-AA, the reaction described above, excluding the addition of Alexa Fluor 350 was performed. The molecular weight of conjugated PDGF-AA-MPBH was determined using MALDI-TOF.

Using MALDI-TOF mass spectroscopy, the peak molar mass of PDGF-AA was measured at 25,200 g/mol. After chemical modification, the peak molar mass of PDGF-AA-MPBH was 26,251 g/mol, confirming the successful reaction with MPBH. PDGF-AA was modified with Alexa-350 and MPBH (MI-PDGF-AA); the UV absorbance at 280 nm of PDGF-AA overlapped with the fluorescence at 345 nm of Alexa-350, when eluted on the FPLC, confirming the successful reaction of PDGF-AA with Alexa 350.

In order to test bioactivity, MI-PDGF-AA was added to NSPC cultures and compared to unmodified PDGF-AA in terms of the NSPC differentiation to oligodendrocytes. After 7 days of culture, 58±8.8% and 61±4.7% of NSPCs differentiated into RIP-positive cells in the presence of unmodified PDGF-AA and MI-PDGF-AA, respectively (n=3). These RIP-positive cells exhibited oligodendrocytic morphologies having slender processes radiating out from their cell bodies. These data demonstrate that MI-PDGF-AA retained bioactivity relative to unmodified PDGF-AA.

Agarose was modified with S-2-nitrobenzyoyl chloride (NBC) which yielded agarose-thiol after exposure to UV light. MI-PDGF-AA was added to agarose-thiol where a Michael-type addition occurred between the thiol and maleimide, yielding agarose-PDGF-AA. By comparison to a standard curve of fluorescent intensity, 210±8 ng of MI-PDGF-AA was immobilized to agarose-SH. When MI-PDGF-AA was reacted with agarose-S-NBC (without deprotection), 30±10 ng of physically adsorbed MI-PDGF-AA was detected. Together these data demonstrated that ~86% of MI-PDGF-AA was covalently-bound to agarose and ~14% was physically adsorbed.

Figure 11:
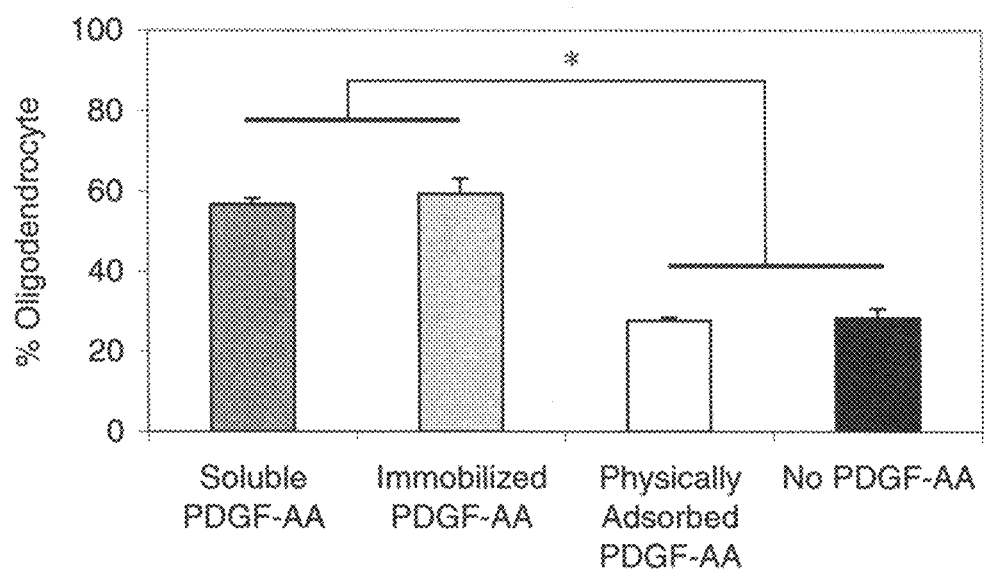
FIG. 11 illustrates the comparison of the relative distribution (%) of RIP positive cells among soluble platelet-derived growth factor (PDGF) PDGF-AA, immobilized PDGF-AA, physically adsorbed PDGF-AA, and no PDGF-AA treatments (* shows statistical significance measured by ANOVA. p<0.0001). The total cell number between soluble PDGF-AA vs. immobilized PDGF-AA was not significantly different (n=3)

To test the ability of immobilized PDGF-AA to promote differentiation of NSPCs, 210 ng/well of PDGF-AA was immobilized to agarose hydrogel surfaces and compared to agarose hydrogels with either soluble, adsorbed or no MI-PDGF-AA in terms of NSPC differentiation to RIP-positive cells. Since it was difficult to quantify differentiation of cells cultured on agarose, NSPCs were cultured on laminin-coated glass cover slips which were then covered with agarose hydrogels. After 7 d of culture, cells were immunostained for RIP (immunochemical marker for oligodendrocytes) and the percentage of RIP-positive cells was compared between the different groups. Agarose-immobilized PDGF-AA showed a similar percentage of RIP-positive cells (57±1.5%) to soluble PDGF-AA controls (59±3.8%), which was not significantly different (n=3). NSPCs cultured in the presence of physically adsorbed PDGF-AA agarose showed a similar differentiation profile to RIP-positive cells (27±0.7%) as control cells cultured in the absence of PDGF-AA (28±2.3%). Physically adsorbed PDGF-AA did not stimulate NSPC differentiation above that of controls; however, chemically immobilized PDGF-AA maintained bioactivity and resulted in a similar percentage of RIP-positive cells as soluble PDGF-AA (FIG. 11). Different oligodendrocyte morphologies were observed for NSPCs cultured in the presence of immobilized PDGF-AA vs. soluble PDGF-AA.

With the goal of culturing NSPCs directly on agarose hydrogel matrices, agarose was modified with the ubiquitous cell adhesive ligand, GRGDS, binding agarose thiol with GRGDS-maleimide). NSPCs were cultured on agarose GRGDS and tested for multipotentiality in the presence of 5% FBS after 5 d in culture. Cells were immunostained with β-III tubulin (a marker for neurons), GFAP (for astrocytes) and RIP (for oligodendrocytes). The multipotentiality of these NSPCs cultured on agarose-GRGDS was demonstrated, where cells immunostained positively for βIII tubulin, GFAP and RIP. Interestingly, when NSPCs were cultured on agarose hydrogels that lacked immobilized GRGDS, the NSPCs survived yet formed large aggregates in suspension, confirming the importance of GRGDS-modified agarose for cell adhesion and subsequent differentiation.

NSPCs were cultured on agarose-PDGF-AA samples and shown to differentiate preferentially to oligodendrocytes as demonstrated by qPCR and immunocytochemistry. This demonstrates that immobilized growth factors can stimulate stem/progenitor cell differentiation similarly to soluble factors; and that the immobilized growth factors can spatially guide NSPC differentiation in 3-dimensions by combining the spatial resolution possible with multiphoton patterning.

Figure 12A:
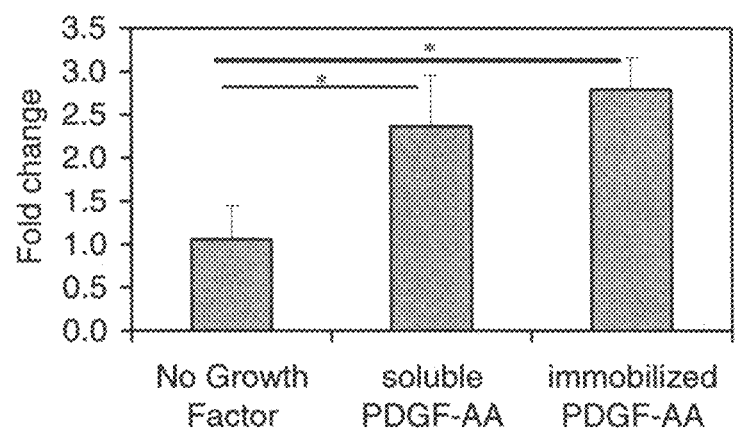
FIG. 12 illustrates the quantitative change in expression of neural cell fate determinants in neural stem/progenitor cells (NSPCs). NSPCs were plated on GRGDS (glycine-arginine-glycine-aspartic acid-serine peptide) agarose hydrogel with immobilized PDGF-AA soluble PDGF-AA, or no PDGF-AA for 5 days. mRNA was prepared and quantitative reverse transcription-polymerase chain reaction was performed. Data are expressed as relative mRNA concentration (DDCt) with respect to the control (no PDGF-AA treatment) for (A) CNPase, (B)—III tubulin, and (C) MOG (* show statistical significance measured by ANOVA, CNPase p<0.0004, MOG p<0.01, mean±STD for triplicate samples).
Figure 12B:
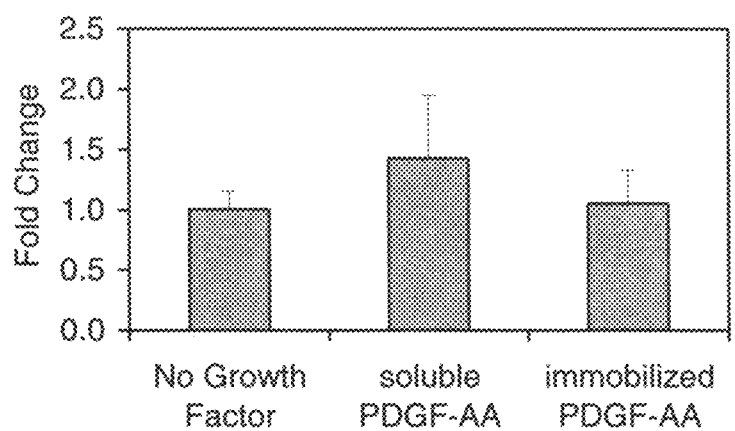
Figure 12C:
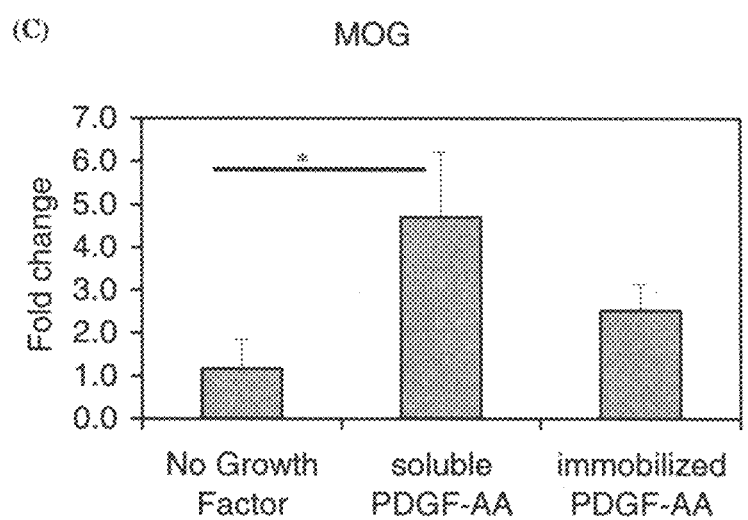

The differentiation of NSPCs was investigated by immunohistochemistry and real-time RT-PCR on agarose hydrogels with either immobilized or soluble MI-PDGF-AA. NSPCs that were plated on GRGDS-agarose hydrogels with immobilized PDGF-AA preferentially differentiated to RIP-positive cells with few β-III tubulin positive cells and no GFAP-positive cells. A similar differentiation profile, NSPCs preferentially differentiated to RIP-positive cells, was observed for NSPCs cultured on GRGDS-agarose hydrogel in the presence of soluble PDGF-AA. To determine the level of gene expression in differentiated cells, oligodendrogenic specific mRNA markers, CNPase and MOG, the neuronal marker, β-III tubulin and the astrogenic marker, GFAP, were quantified using real-time RT-PCR. To facilitate comparison between soluble and immobilized PDGF-AA, data were normalized to controls of NSPCs cultured on GRGDS-agarose hydrogel in the absence of serum and PDGF-AA for 5 d. NSPCs cultured on both immobilized PDGF-AA or soluble agarose showed a similar 2.5-fold increase in CNPase mRNA levels compared to controls (FIG. 12A). NSPCs cultured on GRGDS-agarose in the presence of both soluble and immobilized PDGF-AA expressed similar amount of mRNA expression levels of β-III tubulin as controls (FIG. 12B) and GFAP expression was not detected in any of the samples. It has been found that the MOG mRNA level of NSPCs cultured in the presence of soluble PDGF-AA was significantly greater than that of NSPCs cultured on immobilized PDGF-AA which, in turn, was not significantly different from controls (FIG. 12C). Taken together, the mRNA and immunohistochemical markers demonstrate that immobilized PDGF-AA on GRGDS-agarose hydrogel promotes oligodendrogenic differentiation.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

REFERENCES

1. Denk, W.; Strickler, J. H.; Webb, W. W. *Science* 1990, 248, 73.

2. Recent reviews: (a) Helmchen, F.; Denk, W. *Nature Methods* 2005, 2, 932. (b) Diaspro, A.; Chirico, G.; Collini, M. Q. *Rev. Biophys.* 2005, 38, 97. (c) Svoboda, K.; Yasuda, R. *Neuron* 2006, 50, 823. (d) Rubart, M. *Circ. Res.* 2004, 95, 1154.
3. For example, see: (a) Cumpston, B. H., et al. *Nature* 1999, 398, 51. (b) Lu, Y.; Hasegawa, F.; Goto, T.; Ohkuma, S.; Fukuhara, S.; Kawazu, Y.; Totani, K.; Yamashita, T.; Watanabe, T. *J. Mater. Chem.* 2004, 14, 75. (c) Kuebler, S. M.; Braun, K. L.; Zhou, W.; Cammack, J. K.; Yu, T.; Ober, C. K.; Marder, S. R.; Perry, J. W. *J. Photochem. Photobiol. A* 2003, 158, 163.
4. (a) Hill, R. T.; Lyon, J. L.; Allen, R.; Stevenson, K. J.; Shear, J. B. *J. Am. Chem. Soc.* 2005, 127, 10707. (b) Allen, R.; Nielson, R.; Wise, D. D.; Shear, J. B. *Anal. Chem.* 2005, 77, 5089. (c) Kaehr, B.; Allen, R.; Javier, D. J.; Currie, J.; Shear, J. B. *Proc. Natl. Acad. Sci. USA* 2004, 101, 16104.
5. (a) Basu, S.; Cunningham, L. P.; Pins, G. D.; Bush, K. A.; Taboada, R.; Howell, A. R.; Wang, J.; Campagnola, P. J. *Biomacromolecules* 2005, 6, 1465. (b) Basu, S.; Wolgemuth, C. W.; Campagnola, P. J. *Biomacromolecules* 2004, 5, 2347.
6. (a) Luo, Y.; Shoichet, M. S, *Nature Materials* 2004, 3, 249. (b) Luo, Y.; Shoichet, M. S. *Biomacromolecules* 2004, 5, 2315.
7. Musoke, P.; Shoichet, M. S. *Biomed. Mater.* 2006, 1, 162 (this reference is specifically not acknowledged as prior art to the present application).
8. Furuta, T.; Wang, S. S.-H.; Dantzker, J. L.; Dore, T. M.; Bybee, W. J.; Callaway, E. M.; Denk, W.; Tsien, R. Y. *Proc. Natl. Acad. Sci. USA* 1999, 96, 1193.
9. Suzuki, A. Z.; Watanabe, T.; Kawamoto, M.; Nishiyama, K.; Yamashita, H.; Ishii, M.; Iwamura, M.; Furuta, T. *Org. Lett.* 2003, 5, 4867.
10. Lu, M.; Fedoryak, O. D.; Moister, B. R.; Dore, T. M. *Org. Lett.* 2003, 5, 2119.
11. Lin, W.; Lawrence, D. S. *J. Org. Chem.* 2002, 67, 2723.
12. (a) Schade, B.; Hagen, V.; Schmidt, R.; Herbrich, R.; Krause, E.; Eckardt, T.; Bendig, J. *J. Org. Chem.* 1999, 64, 9109. (b) Eckardt, T.; Hagen, V.; Schade, B.; Schmidt, R.; Schweitzer, C.; Bendig, J. *J. Org. Chem.* 2002, 67, 703.
13. (a) Goard, M.; Aakalu, A.; Fedoryak, O. D.; Quinonez, C.; St. Julien, J.; Poteet, S. J.; Schuman, E. M.; Dore, T. M. *Chem. Biol.* 2005, 12, 685. (b) Perdicakis, B.; Montgomery, H. J.; Abbott, G. L.; Fishlock, D.; Lajoie, G. A.; Guillemette, J. G.; Jervis, E. *Bioorg. Med. Chem.* 2005, 13, 47. (c) Ando, H.; Furuta, T.; Tsien, R. Y.; Okamoto, H. *Nature Genetics* 2001, 28, 317.
14. (a) Hahn, M. S.; Miller, J. S.; West, J. L. *Adv. Mater.* 2006, 18, 2679. (b) Albrecht, D. R.; Underhill, G. H.; Wassermann, T. B.; Sah, R. L.; Bhatia, S, N. *Nature Methods* 2006, 3, 369. (c) Flaim, C. J.; Chien, S.; Bhatia, S, N. *Nature Methods* 2005, 2, 119.
15. Zipfel, W. R.; Williams, R. M.; Webb, W. W. *Nat. Biotechnol.* 2003, 21, 1369

APPENDIX

```
Sub PatternGrid()
'This macro assumes you have defined a small ROI, zoomed
in on it (with the RoiZ button), and turned the laser
power up.
'By doing this, you define a shape to be "stamped" in
your sample at regular intervals (a three-dimensional
grid of your shape).
'The macro asks for the number of rows, columns and
levels in your grid, and the spacing along all three
axes. (Make sure you have room in your sample!)
'It also asks for the number of scans over each
individual shape. The optimum value for this depends on
your laser power, etc.
'This version of the macro uses frame averaging to scan
over one shape an arbitrary number of times. An earlier
version used a time series
'(i.e., tell the scanner to take a series of n images,
separated 500ms apart). I believe the frame averaging
method is faster and doesn't fill up the
'hard disk as fast (time series scans generate a lot of
data).

Dim nr As Integer    'Number of rows in the pattern
    Dim nc As Integer    'Number of columns in the pattern
    Dim nl As Integer    'Number of levels (z) in the
pattern Dim Scans As Long    'Number of scans over each
individual shape
    Dim ir As Integer    'Counting variable for rows
    Dim ic As Integer    'Counting variable for columns
    Dim il As Integer    'Counting variable for levels Dim xspacing As Double  'Spacing of rows
    Dim yspacing As Double  'Spacing of columns
    Dim zspacing As Double  'Spacing of levels Dim xorigin As Double  'These variables hold the
original xyz position so that the microscope can move
back to the origin
    Dim yorigin As Double  'at the end of the pattern.
    Dim zorigin As Double Dim xp As Double  'These variables are to hold the
stage xyz position for calculating where the next point
should go.
    Dim yp As Double  'If the SetPosRelXYZ command
```

```
      DOCSTOR-#1268296-v1-Patent_Script_Document.TXT
actually worked, we wouldn't need them.
    Dim zp As Double 'Dim DeltaT As LCSTime    'I have commented out these
three variables. They were needed when the macro used
time series to stamp each shape.
    'Dim CompleteTime As LCSTime
    'Dim PatternTime As Double Dim tStart As Double 'These variables are used to
inform the user, when the macro is finished, how long the
whole thing took.
    Dim tEnd As Double MsgBox ("This program stamps a pattern -- which you
have already defined as a ROI -- at set intervals in
space. Click OK to continue.")

nr = Val(InputBox("How many rows in the pattern?",
"", 5))
    nc = Val(InputBox("How many columns in the pattern?",
"", 5))
    nl = Val(InputBox("How many levels in the pattern?",
"", 5))

Scans = Val(InputBox("How many scans on each point?",
"", 60))

'Stage position values need to be fed to the
microscope in meters, but it is more convenient to enter
spacings in microns.
    'The lines below get the values in microns and
immediately convert them to meters.
    xspacing = Val(InputBox("Enter the spacing (in
microns) between rows.", "", 0.0002)) / 1000000
    yspacing = Val(InputBox("Enter the spacing (in
microns) between columns.", "", 0.0002)) / 1000000
    zspacing = Val(InputBox("Enter the spacing (in
microns) between levels.", "", 0.0002)) / 1000000

'Scanner.Scanmode = "xyt"    'Commented out these two
lines. They were needed when time series were used to run
the macro.
    'DeltaT.Milliseconds = 500

'Scanner.SetTimePeriode DeltaT, Scans, CompleteTime,
eCompleteTimeCalculation    'This was used to set the time
```

DOCSTOR-#1268296-v1-Patent_Script_Document.TXT
series parameters. No longer needed.
    Application.Scanner.AverageFrame = Scans 'Sets Frame Averaging to scan multiple times over one frame Hardware.Microscope.Stage.GetPosXYZ xorigin, yorigin, zorigin 'Gets the original position of the stage
    zorigin = Hardware.ZPosZDrive 'Gets the z position of the stage (the Z in GetPosXYZ is just a dummy and always returns 0)

MsgBox ("A total of " + Str(nc * nr * nl) + " points will be stamped, with " + Str(Scans) + " scans per point.")
    tStart = Timer 'tstart is a counting variable for the beginning of the pattern stamp. It's just to help let the user know how long the pattern took.

Hardware.Microscope.Stage.GetPosXYZ xp, yp, zp 'These variables are now set to the stage position.

For il = 1 To nl    'Levels loop

For ir = 1 To nr    'Rows loop

For ic = 1 To nc    'Columns loop

Hardware.Microscope.Stage.SetPosXYZ xp, yp, zp    'Move the stage to the current xp, yp, zp values 'tEnd = Timer + 2          'These three lines can be un-commented to test the operation of the script
                'while Timer < tEnd 'They make a 2-s pause for testing purposes -- you can comment out the actual scan command
                'Wend                       'to test the stage movements without touching your sample.

'Scanner.StartSeriesScan True    'This was the command used to stamp a shape when the time series method was used.
                Application.Scanner.StartSingleScan True 'Instructs the confocal to make a single scan.
                'Since Frame Averaging is on, the number of scans over this point is dictated by the variable "Scans" (see above).

DOCSTOR-#1268296-v1-Patent_Script_Document.TXT

```
        Hardware.Microscope.Stage.GetPosXYZ xp, yp, zp 'Refresh the variables xp, yp, zp
        xp = xp + xspacing 'Increment xp by the spacing value
        Hardware.Microscope.Stage.SetPosXYZ xp, yp, zp 'Set the stage to the updated position.
        Beep 'Beeps after every point has been stamped.

Next ic

Hardware.Microscope.Stage.GetPosXYZ xp, yp, zp 'Refresh the variables xp, yp, zp
        xp = xp - (nc * xspacing) 'Reset xp to the beginning of the row
        yp = yp + yspacing 'Increment yp by the spacing value
        Hardware.Microscope.Stage.SetPosXYZ xp, yp, zp 'Set the new stage position
        Beep 'Beeps at the end of a row as well. After the last shape in a row, the user will hear two beeps.

Next ir yp = yp - (nr * yspacing) 'Reset yp to the beginning of the column.
        Hardware.ZPosZDrive = zorigin + (il * zspacing) 'Move the z axis by the correct increment
        Beep 'Beeps at the end of a level. After an entire level has been completed, the user will hear three beeps.

Next il

Application.Scanner.AverageFrame = 1 'Sets frame averaging back to 1.
    Hardware.Microscope.Stage.SetPosXYZ xorigin, yorigin, zorigin 'Sets the stage XY position back to where it started.
    Hardware.ZPosZDrive = zorigin 'Sets the Z position back to where it started.
    MsgBox ("Done! The whole thing took " + Str(Timer - tStart) + " seconds.") 'Message box when the pattern is finished.

End Sub
```

DOCSTOR-#1268296-v1-Patent_Script_Document.TXT

```
Sub MakeGradient()
'This macro is very useful for defining the parameters of
a patterning project. We've used it a lot in the Shoichet
group.
'It is conceptually similar to PatternGrid, but makes
only one line, and allows the user to determine how many
scans occur on each stamped shape.
'This makes it useful for optimizing scan numbers, laser
power, etc.
'It can also be used to make linear gradients. If the
spacing between stamped shapes is equal to the width of
the shape you are stamping, you will
'end up with a "step wedge" of shapes jammed one against
the other, each one "darker" than the previous. If these
shapes (and the spacing) are very thin,
'you end up with a smooth gradient.

Dim InitialScans As Integer 'The number of scans on
the first stamped shape
    Dim ScanStep As Integer 'How many scans to increment
on going to the next shape
    Dim StepNums As Integer 'How many shapes to stamp
    Dim Scans As Long 'Will be used to set the number of
scans for the current stamping action Dim xp As Double 'Variables for storing the current
xyz position
    Dim yp As Double
    Dim zp As Double Dim SpaceIncrement As Double 'The spacing between
adjacent shapes in the gradient
    Dim i As Integer 'A counting variable InitialScans = Val(InputBox("What is the starting
number of scans?", "Starting scan number", "1"))
    ScanStep = Val(InputBox("How many scans to add in
each element of the gradient?", "Gradient slope", "2"))
    StepNums = Val(InputBox("How many steps in the
gradient?", "Number of steps", "10"))

SpaceIncrement = Val(InputBox("What is the spacing
between gradient elements (in meters)?", "Gradient
spacing", "0.0002"))

'Create the gradient
    For i = 1 To StepNums
```

DOCSTOR-#1268296-v1-Patent_Script_Document.TXT

```
        Scans = InitialScans + ((i - 1) * ScanStep) 'Set the number of scans
        Application.Scanner.AverageFrame = Scans 'Sets Frame Averaging to the correct value
        Scanner.StartSingleScan True 'Stamps the shape Hardware.Microscope.Stage.GetPosXYZ xp, yp, zp 'Move stage over by the increment
        xp = xp + SpaceIncrement
        Hardware.Microscope.Stage.SetPosXYZ xp, yp, zp Next i Hardware.Microscope.Stage.GetPosXYZ xp, yp, zp
    xp = xp - (SpaceIncrement * StepNums)
    Hardware.Microscope.Stage.SetPosXYZ xp, yp, zp
    Application.Scanner.AverageFrame = 1 'Sets Frame Averaging back to 1.
    MsgBox ("Done! Moved you back to where you began.")

End Sub

Sub ZColumn()
'This macro builds up a patterned "column" by stacking patterns of the same planar shape one on top of the other up the z-axis, at regular intervals.
'Like PatternGrid, it assumes that the user has defined an ROI, zoomed in on it, turned the laser power up, etc.
'
    Dim ColLength As Long 'Total height of the column to be created
    Dim Elements As Integer 'The macro will calculate how many planar shapes need to be stacked to create the column
    Dim Scans As Long 'Number of scans on each planar shape
    Dim i As Integer 'Counting variable
    Dim Displacement As Double 'Spacing between planar shapes in the column. With the 20x/0.5 objective, 10-12 microns is appropriate.
    Dim z As Double 'Positional variable to set Z-stage position Dim zorigin As Double 'Z-stage starting position
    Dim PatternTime As Double 'Counting variable to let the user know how long it took to create the pattern.
```

DOCSTOR-#1268296-v1-Patent_Script_Document.TXT

```
    MsgBox ("Current Z Position: " + Str((Hardware.ZPosZDrive) * 1000000) + ". The macro will start from this position and move up.")
    zorigin = Hardware.ZPosZDrive 'ZPosZDrive is confusing because you can both read from it (what's the current stage position?) and set it ColLength = Val(InputBox("What is the total height of the column you wish to make, in microns?"))
    Scans = Val(InputBox("How many scans on each element?"))
    Displacement = Val(InputBox("How closely spaced should the column elements be, in microns?"))

Elements = Int(ColLength / Displacement) 'Calculates how many planar shapes need to be stacked on one another. It has to be an integral number, hence "int".

Displacement = Displacement / 1000000 'Convert to meters

Application.Scanner.AverageFrame = Scans 'Sets frame averaging value to control the number of scans on each step of the column.

For i = 1 To Elements z = Hardware.ZPosZDrive 'Sets z to equal the current Z position
        Application.Scanner.StartSingleScan True 'Make the planar shape
        z = z + Displacement 'Increment z by the spacing value
        Hardware.ZPosZDrive = z 'Move the stage Z position to the newly calculated Z Next i MsgBox ("Done! Current z position is " + Str((Hardware.ZPosZDrive) * 1000000) + ". Click OK to return to the original position and exit.")
    Hardware.ZPosZDrive = zorigin 'Sets the stage Z position back to where it started.
    Application.Scanner.AverageFrame = 1 'Sets frame averaging back to 1.

End Sub
```

DOCSTOR-#1268296-v1-Patent_Script_Document.TXT

```
Sub RowOfZColumns()
'This macro basically repeats the ZColumn macro at set
space intervals. It can end up taking a long time to
complete, so be forewarned.

Dim ColLength As Long 'Total height of the column to
be created
    Dim Elements As Integer 'The macro will calculate how
many planar shapes need to be stacked to create the
column
    Dim Scans As Long 'Number of scans on each planar
shape
    Dim i As Integer 'Counting variable
    Dim Displacement As Double 'Spacing between planar
shapes in the column. With the 20x/0.5 objective, 10-12
microns is appropriate.
    Dim z As Double 'Positional variable to set Z-stage
position
    Dim ic As Integer 'Counting variable for adjacent
columns Dim xp As Double 'Position variables for making
adjacent columns
    Dim yp As Double
    Dim zp As Double Dim ColSpacing As Double 'Spacing between adjacent
columns
    Dim ColNumber As Integer 'Number of columns to create
    Dim zorigin As Double 'Z-stage starting position
    Dim PatternTime As Double 'Counting variable to let
the user know how long it took to create the pattern.

MsgBox ("Current Z Position: " +
Str((Hardware.ZPosZDrive) * 1000000) + ". The macro will
start from this position and move up for each column.")
    zorigin = Hardware.ZPosZDrive 'ZPosZDrive is
confusing because you can both read from it (what's the
current stage position?) and set it ColLength = Val(InputBox("What is the total height of
the column you wish to make, in microns?"))
    Scans = Val(InputBox("How many scans on each
element?"))
    Displacement = Val(InputBox("How closely spaced
should the column elements be, in microns?"))
```

```
    DOCSTOR-#1268296-v1-Patent_Script_Document.TXT
    ColNumber = Val(InputBox("How many adjacent columns
would you like to make?"))
    ColSpacing = Val(InputBox("What is the spacing
between adjacent columns, in microns?"))

Elements = Int(ColLength / Displacement) 'Calculates
how many planar shapes need to be stacked on one another.
It has to be an integral number, hence "int".

Displacement = Displacement / 1000000 'Convert to
meters
    ColSpacing = ColSpacing / 1000000 'Convert to meters Application.Scanner.AverageFrame = Scans 'Sets frame
averaging value to control the number of scans on each
step of the column.

For ic = 1 To ColNumber

For i = 1 To Elements z = Hardware.ZPosZDrive 'Sets z to equal the
current Z position
        Application.Scanner.StartSingleScan True
'Make the planar shape
        z = z + Displacement 'Increment z by the
spacing value
        Hardware.ZPosZDrive = z 'Move the stage Z
position to the newly calculated Z Next i Beep
    Hardware.ZPosZDrive = zorigin
    Hardware.Microscope.Stage.GetPosXYZ xp, yp, zp
'Move stage over by the increment
    xp = xp + ColSpacing
    Hardware.Microscope.Stage.SetPosXYZ xp, yp, zp Next ic MsgBox ("Done! Current z position is " +
Str((Hardware.ZPosZDrive) * 1000000) + ". Click OK to
return to the original position and exit.")
    Hardware.ZPosZDrive = zorigin 'Sets the stage Z
position back to where it started.
    Application.Scanner.AverageFrame = 1 'Sets frame
averaging back to 1.
```

DOCSTOR-#1268296-v1-Patent_Script_Document.TXT

```
    xp = xp - (ic * SpaceIncrement)
    Hardware.Microscope.Stage.SetPosXYZ xp, yp, zp End Sub Sub Spiral()
'I will document and comment this later.

Dim xorigin As Double
    Dim yorigin As Double
    Dim zorigin As Double
    Dim zpitch As Double Dim xp As Double
    Dim yp As Double
    Dim zp As Double Dim radius As Double Dim wind As Double Dim DeltaT As LCSTime
    Dim CompleteTime As LCSTime
    Dim PatternTime As Double Dim tStart As Double
    Dim tEnd As Double
    Dim Scans As Long MsgBox ("This program writes a spiral through space -- which you have already defined as a ROI -- Click OK to continue.")

nc = Val(InputBox("How many steps in the spiral?", "", 30))
    nr = Val(InputBox("How many complete revolutions?", "", 1))
    radius = Val(InputBox("What is the radius of the spiral, in microns?", "", 300)) / 1000000
    Scans = Val(InputBox("How many scans on each step?", "", 3))
    zpitch = Val(InputBox("What is the helical pitch, in microns?", "", 400)) / 1000000

Scanner.Scanmode = "xyt"
    DeltaT.Milliseconds = 500
    Hardware.Microscope.Stage.GetPosXYZ xorigin, yorigin,
```

```
    DOCSTOR-#1268296-v1-Patent_Script_Document.TXT
zorigin

Scanner.SetTimePeriode DeltaT, Scans, CompleteTime,
eCompleteTimeCalculation
    Hardware.Microscope.Stage.GetPosXYZ xorigin, yorigin,
zorigin
    zorigin = Hardware.ZPosZDrive tStart = Timer
    wind = 0

For ic = 1 To nc * nr   'Steps loop xp = xorigin + radius * (Cos(wind))
        yp = yorigin + radius * (Sin(wind))

Hardware.Microscope.Stage.SetPosXYZ xp, yp, zp
'Move the stage by the row spacing 'tEnd = Timer + 4      'Comment these three lines
out for real operation
        'While Timer < tEnd
        'Wend      'These two lines make a 5-s pause for
testing purposes Scanner.StartSeriesScan True   'Comment this out
for tests Hardware.Microscope.Stage.GetPosXYZ xp, yp, zp Beep
        wind = wind + ((3.14159 * 2 * nr) / nc)

Hardware.ZPosZDrive = zorigin + (ic * (zpitch /
nc))

Next ic

Beep
    Hardware.Microscope.Stage.SetPosXYZ xorigin, yorigin,
zp
    Hardware.ZPosZDrive = zorigin
    MsgBox ("Done! The whole thing took " + Str(Timer -
tStart) + " seconds. Moved back to origin.")

End Sub
```

What is claimed:

1. A three-dimensional hydrogel body, the hydrogel comprising:
    a plurality of multiphoton photocleavable molecules bound within said hydrogel body, each molecule comprising a multiphoton-labile protective group and a protected group, wherein the protective group is cleavable upon multiphoton excitation to deprotect the protected group, without causing substantial polymerization of the hydrogel;
    wherein the multiphoton photocleavable molecule is selected from the group consisting of a coumarin-protected molecule, a 7-nitroindoline-protected molecule, and a p-hydroxyphenacyl-protected molecule.

2. The hydrogel body of claim 1 wherein the multiphoton photocleavable molecule is 4-((2-aminoethylthio)methyl)-6-bromo-7-hydroxy-2H-chromen-2-one.

3. The hydrogel body of claim 1 wherein the multiphoton photocleavable molecule is 6-bromo-7-hydroxy-2-oxo-2H-chromen-4-yl(methyl 2-aminoethylcarbamate).

4. The hydrogel body of claim 1 wherein the hydrogel is selected from agarose, hyaluronan, polyethylene glycol (PEG) and derivatives thereof, alginate, and dextran and derivatives thereof.

5. A chemically patterned hydrogel body comprising:
    the hydrogel body according to claim 1, having multiphoton photocleavable molecules bound therein, each molecule comprising a multiphoton-labile protective group and a protected group, wherein the protective groups are cleavable upon multiphoton excitation to deprotect the protected groups without causing substantial polymerization of the hydrogel, wherein a portion thereof comprises groups deprotected by exposure to multiphoton excitation, said deprotected groups forming at least one pattern that can be controlled with independent x-, y-, and z-dimension control;
    wherein the deprotected groups are thiol groups, each thiol group being capable of undergoing a reaction following cleavage of the protective group selected from the group consisting of a Michael-type addition reaction, a $SN_2$ displacement reaction, and a disulfide bond formation.

6. The chemically patterned hydrogel body of claim 5 wherein the reaction occurs between the thiol group and a molecule bearing an unsaturated imide functional group.

7. The chemically patterned hydrogel body of claim 6 wherein the unsaturated imide functional group is maleimide.

8. A chemically patterned hydrogel body comprising:
    the hydrogel body according to claim 1, having multiphoton photocleavable molecules bound therein, each molecule comprising a multiphoton-labile protective group and a protected group, wherein the protective groups are cleavable upon multiphoton excitation to deprotect the protected groups without causing substantial polymerization of the hydrogel, wherein a portion thereof comprises groups deprotected by exposure to multiphoton excitation, said deprotected groups forming at least one pattern that can be controlled with independent x-, y-, and z-dimension control;
    wherein the deprotected groups react with bioactive molecules each having a reactive functional group following cleavage of the protective group.

9. The chemically patterned hydrogel body of claim 8 wherein the bioactive molecules are selected from the group consisting of a protein, a peptide, a polysaccharide, a drug, a growth factor, an enzyme, a hormone, a vitamin, a gene and a small molecule.

10. The chemically patterned hydrogel body of claim 9 wherein the bioactive molecules are selected from the group comprising biotin, laminin, fibronectin, collagen, a peptide mimetic, a RGD peptide, a RGD peptide derivative, a YIGSR peptide, a YIGSR derivative, an IKVAV peptide, an IKVAV derivative, a growth factor, and a small molecule capable of inducing adhesion or differentiation of a mammalian cell.

11. The chemically patterned hydrogel body of claim 8 wherein the bioactive molecules are covalently immobilized to the hydrogel.

12. The chemically patterned hydrogel body of claim 8 wherein the bioactive molecules are each modified with a maleimide functional group.

13. The chemically patterned hydrogel body of claim 8 wherein the bioactive molecules stimulate one or more of cell adhesion, cell differentiation and cell growth.

14. The chemically patterned hydrogel body of claim 13 further comprising dispersed cells, wherein the cells are selected from the group consisting of mammalian stem cells and mammalian progenitor cells.

15. The chemically patterned hydrogel body of claim 14 wherein the mammalian stem cells are selected from the group consisting of adult or embryonic mammalian stem cells and mammalian progenitor cells derived from a tissue selected from the group consisting of brain, retina, mesenchyme, hematopoetic, cardiac, skin, bone, nervous system, cartilage, vasculature and umbilical cord blood.

16. A method of chemically patterning a 3-dimensional hydrogel body, the hydrogel comprising multiphoton photocleavable molecules bound within said hydrogel, each molecule comprising a multiphoton-labile protective group and a protected group, wherein each protective group is cleavable upon multiphoton excitation to deprotect the protected group providing a plurality of deprotected protected groups that form patterns in the hydrogel, without causing substantial polymerization of the hydrogel, the method comprising:
    irradiating the hydrogel with pulsed light for multiphoton excitation to deprotect a portion of the protected groups.

17. The method of claim 16 further comprising the step of delineating a geometric region to be patterned by irradiation.

18. The method of claim 16 further comprising exposing the modified hydrogel to a biomolecule that binds to the deprotected groups either before or after irradiating the modified hydrogel, the biomolecule having a bound tag that allows visualization; and washing the hydrogel and visualizing the bound tag.

19. The method of claim 16 further comprising the step of raster-scanning of a laser focal point within a plane set to a desired depth below a surface of the modified hydrogel.

20. A multiphoton photocleavable molecule consisting of 4-((2-aminoethylthio)methyl)-6-bromo-7-hydroxy-2H-chromen-2-one.

21. The method of claim 16, wherein the multiphoton excitation is localized to a focal point of a laser used to provide the multiphoton excitation, said laser being controllable with independent x-, y-, and z-dimension control of the focal point of the laser providing the multiphoton excitation.

* * * * *